United States Patent
Cohen et al.

(10) Patent No.: US 11,154,228 B2
(45) Date of Patent: Oct. 26, 2021

(54) ELECTRODE USE INDICATION

(71) Applicant: ZOLL Medical Corporation, Chelmsford, MA (US)

(72) Inventors: Robert M. Cohen, Pittsburgh, PA (US); Gregory R. Frank, Mt. Lebanon, PA (US)

(73) Assignee: ZOLL Medical Corporation, Chelmsford, MA (US)

( * ) Notice: Subject to any disclaimer, the term of this patent is extended or adjusted under 35 U.S.C. 154(b) by 911 days.

(21) Appl. No.: 15/249,616

(22) Filed: Aug. 29, 2016

(65) Prior Publication Data
US 2017/0056650 A1    Mar. 2, 2017

Related U.S. Application Data

(60) Provisional application No. 62/212,451, filed on Aug. 31, 2015.

(51) Int. Cl.
| | | |
|---|---|---|
| *A61B 5/25* | (2021.01) | |
| *A61N 1/04* | (2006.01) | |
| *A61B 5/00* | (2006.01) | |
| *A61N 1/36* | (2006.01) | |

(52) U.S. Cl.
CPC .............. *A61B 5/25* (2021.01); *A61B 5/6804* (2013.01); *A61B 5/68335* (2017.08); *A61N 1/0484* (2013.01); *A61N 1/0492* (2013.01); *A61N 1/3603* (2017.08); *A61N 1/046* (2013.01); *A61N 1/0456* (2013.01)

(58) Field of Classification Search
CPC . A61B 5/0402; A61B 5/0408; A61B 5/04082; A61B 5/04087; A61B 5/0415; A61B 5/0424; A61B 5/053; A61B 5/0531; A61B 5/0533; A61B 5/6801; A61B 5/6802; A61B 5/6804; A61B 5/6805; A61B 5/6813; A61B 5/6823; A61B 5/6831; A61B 5/6832; A61B 5/6833; A61B 5/68335

See application file for complete search history.

(56) References Cited

U.S. PATENT DOCUMENTS

| | | | |
|---|---|---|---|
| 5,697,955 A | 12/1997 | Stolte | |
| 6,611,709 B2 | 8/2003 | Faller | |
| 7,526,345 B2 | 4/2009 | Covey et al. | |
| 8,116,864 B2 | 2/2012 | Covey et al. | |
| 8,280,481 B2* | 10/2012 | Copp | A61B 5/04087 600/396 |
| 8,565,901 B2 | 10/2013 | Dupelle et al. | |
| 2003/0055478 A1* | 3/2003 | Lyster | A61N 1/0492 607/142 |
| 2012/0158074 A1* | 6/2012 | Hall | A61B 5/024 607/5 |
| 2013/0325096 A1* | 12/2013 | Dupelle | A61N 1/0496 607/142 |
| 2017/0258357 A1* | 9/2017 | Riemenschneider | A61B 5/0492 |

* cited by examiner

*Primary Examiner* — Eun Hwa Kim
(74) *Attorney, Agent, or Firm* — Fish & Richardson P.C.

(57) ABSTRACT

An electrode patch for use with an external medical device, the electrode patch comprising: a first surface configured to be attached to a skin of a patient monitored by the external medical device, and an indicating mechanism disposed on the electrode patch and configured to indicate an end of a predetermined lifespan of the electrode patch.

40 Claims, 15 Drawing Sheets

ELECTRODE USE INDICATION

CLAIM OF PRIORITY

This application claims priority under 35 USC § 119(e) to U.S. Patent Application Ser. No. 62/212,451, filed on Aug. 31, 2015, the entire contents of which are hereby incorporated by reference.

BACKGROUND

This disclosure relates to systems and techniques for indicating electrode use and/or deterioration over a period of time.

There are a wide variety of electronic and mechanical devices for monitoring and treating patients' medical conditions. In some examples, depending on the underlying medical condition being monitored or treated, medical devices such as cardiac pacemakers or defibrillators may be surgically implanted or connected externally to the patient. In some cases, physicians may use medical devices alone or in combination with drug therapies to treat patient medical conditions.

One of the most deadly cardiac arrhythmias is ventricular fibrillation, which occurs when normal, regular electrical impulses are replaced by irregular and rapid impulses, causing the heart muscle to stop normal contractions and to begin to quiver. Normal blood flow ceases, and organ damage or death can result in minutes if normal heart contractions are not restored. Because the victim has no perceptible warning of the impending fibrillation, death often occurs before the necessary medical assistance can arrive. Other cardiac arrhythmias can include excessively slow heart rates known as bradycardia.

Implantable or external pacemakers and defibrillators (such as automated external defibrillators or AEDs) have significantly improved the ability to treat these otherwise life-threatening conditions. Such devices operate by applying corrective electrical pulses directly to the patient's heart. For example, bradycardia can be corrected through the use of an implanted or external pacemaker device. Ventricular fibrillation can be treated by an implanted or external defibrillator.

For example, certain medical devices operate by continuously or substantially continuously monitoring the patient's heart through one or more sensing electrodes for treatable arrhythmias and, when such is detected, the device applies corrective electrical pulses to the heart through one or more therapy electrodes.

SUMMARY

In one aspect, an electrode patch for use with an external medical device includes a first surface configured to be attached to a skin of a patient monitored by the external medical device. The electrode patch also includes an indicating mechanism disposed on the electrode patch and configured to indicate an end of a predetermined lifespan of the electrode patch.

Implementations can include one or more of the following features.

In some implementations, the predetermined lifespan is based on a recommended wear time of the electrode patch.

In some implementations, the indicating mechanism is configured to indicate that the electrode patch should be removed or replaced upon detecting the end of the predetermined lifespan of the electrode patch.

In some implementations, the end of the predetermined lifespan of the electrode patch is determined based on at least one of a use or a duration of use of the electrode patch.

In some implementations, the predetermined lifespan is based on an amount of time that has passed since an initiating event. The initiating event includes at least one of 1) contact between the first surface and skin of a patient, 2) removal of the electrode patch from a packaging 3) removal of the electrode patch from a lining/backing, and 4) a user input.

In some implementations, the electrode patch comprises a removable electrode patch.

In some implementations, the electrode patch comprises an adhesive electrode patch.

In some implementations, the electrode patch comprises one or more electrodes, and wherein the one or more electrodes comprises at least one sensing electrode and at least one therapy electrode.

In another aspect, an external medical device includes an electrode system configured to perform at least one of 1) delivering a therapy to the patient and 2) monitoring a condition of the patient. The external medical device also includes a removable electrode patch configured to communicate signals to or from the electrode system. The external medical device also includes an indicating mechanism configured to indicate that the replaceable electrode patch has reached an end of a predetermined lifespan of the electrode patch.

Implementations can include one or more of the following features.

In some implementations, the predetermined lifespan is based on a recommended wear time of the electrode patch.

In some implementations, the external medical device also includes a controller for controlling the indicating mechanism.

In some implementations, the removable electrode patch includes an adhesive electrode patch.

In another aspect, an electrode patch for use with an external medical device includes a first surface to be disposed on a skin of a patient monitored by the external medical device. The electrode patch also includes an indicating mechanism configured to indicate a measure of an integrity of the electrode patch.

Implementations can include one or more of the following features.

In some implementations, the indicating mechanism is configured to indicate the measure of the integrity of the electrode patch while the electrode patch is disposed on the skin of the patient.

In some implementations, the electrode patch includes a removable electrode patch.

In some implementations, the electrode patch includes an adhesive electrode patch.

In some implementations, the electrode patch includes one or more electrodes. The one or more electrodes include at least one sensing electrode and at least one therapy electrode.

In some implementations, the indicating mechanism is configured to indicate the integrity of the electrode patch based on an underlying condition of at least one of the electrode patch and an interface between the electrode patch and the skin of the patient.

In some implementations, the measure of the integrity of the electrode patch is based on at least one of a signal integrity or a physical integrity.

In some implementations, the underlying condition of the electrode patch includes exposure to a predetermined threshold of moisture.

In some implementations, the measure of the integrity of the electrode patch is determined based on an impedance measured in association with the electrode patch.

In some implementations, the impedance is determined based on a moving average or root mean square.

In some implementations, the indicating mechanism is configured to provide an indication to a user when a difference between impedance of a first sensor and impedance of a second sensor exceeds a predetermined threshold.

In another aspect, an external medical device includes an electrode system configured to perform at least one of 1) delivering a therapy to the patient and 2) monitoring a condition of the patient. The external medical device also includes a removable electrode patch configured to communicate signals to or from the electrode system. The external medical device also includes an indicating mechanism configured to indicate an integrity measure of the electrode patch when the electrode patch is disposed on skin of the patient. The integrity is determined based on an impedance measured in association with the electrode.

Implementations can include one or more of the following features.

In some implementations, the external medical device also includes a garment wearable on a torso of the patient.

In some implementations, the removable electrode patch includes an adhesive electrode patch.

In another aspect, an electrode patch for use with an external medical device includes a first surface configured to be attached to a skin of a patient monitored by the external medical device. The electrode patch also includes an indicating mechanism disposed on the electrode patch and configured to indicate a remaining lifespan of the electrode patch.

Implementations can include one or more of the following features.

In some implementations, the remaining lifespan is based on a predetermined lifespan of the electrode patch.

In some implementations, the remaining lifespan is based on a measure of an integrity of the electrode patch.

In another aspect, a method for indicating when an electrode patch for use with an external medical device should be removed or replaced includes providing an electrode patch that includes a first surface to be disposed on a skin of a patient monitored by the external medical device. The method also includes indicating an end of a predetermined lifespan of the electrode patch.

Implementations can include one or more of the following features.

In some implementations, the electrode patch is configured to be used for a duration of at least 24 hours from when the electrode patch is attached to the skin of the patient. Indicating the end of the predetermined lifespan of the electrode patch includes indicating the end of the duration.

In some implementations, the electrode patch is configured to be used for a duration of at least 48 hours from when the electrode patch is attached to the skin of the patient. Indicating the end of the predetermined lifespan of the electrode patch includes indicating the end of the duration.

In some implementations, the electrode patch is configured to be used for a duration of at least 3 days from when the electrode patch is attached to the skin of the patient. Indicating the end of the predetermined lifespan of the electrode patch includes indicating the end of the duration.

In some implementations, the electrode patch is configured to be used for a duration of at least one week from when the electrode patch is attached to the skin of the patient. Indicating the end of the predetermined lifespan of the electrode patch includes indicating the end of the duration.

In some implementations, the electrode patch is configured to be used for a duration of at least 30 days from when the electrode patch is attached to the skin of the patient. Indicating the end of the predetermined lifespan of the electrode patch includes indicating the end of the duration.

In some implementations, the electrode patch is configured to be used for a cumulative duration of at least 24 hours from when the electrode patch is attached to the skin of the patient. Indicating the end of the predetermined lifespan of the electrode patch includes indicating the end of the cumulative duration.

In some implementations, the electrode patch is configured to be used for a cumulative duration of at least 48 hours from when the electrode patch is attached to the skin of the patient. Indicating the end of the predetermined lifespan of the electrode patch includes indicating the end of the cumulative duration.

In some implementations, the electrode patch is configured to be used for a cumulative duration of at least 3 days from when the electrode patch is attached to the skin of the patient. Indicating the end of the predetermined lifespan of the electrode patch includes indicating the end of the cumulative duration.

In some implementations, the electrode patch is configured to be used for a cumulative duration of at least one week from when the electrode patch is attached to the skin of the patient. Indicating the end of the predetermined lifespan of the electrode patch includes indicating the end of the cumulative duration.

In some implementations, the electrode patch is configured to be used for a cumulative duration of at least 30 days from when the electrode patch is attached to the skin of the patient. Indicating the end of the predetermined lifespan of the electrode patch includes indicating the end of the cumulative duration.

In some implementations, the electrode patch is configured to be used for a duration of at least 24 hours from when the electrode patch is removed from a liner of the electrode patch. Indicating the end of the predetermined lifespan of the electrode patch includes indicating the end of the duration.

In some implementations, the electrode patch is configured to be used for a duration of at least 48 hours from when the electrode patch is removed from a liner of the electrode patch. Indicating the end of the predetermined lifespan of the electrode patch includes indicating the end of the duration.

In some implementations, the electrode patch is configured to be used for a duration of at least 3 days from when the electrode patch is removed from a liner of the electrode patch. Indicating the end of the predetermined lifespan of the electrode patch includes indicating the end of the duration.

In some implementations, the electrode patch is configured to be used for a duration of at least one week from when the electrode patch is removed from a liner of the electrode patch. Indicating the end of the predetermined lifespan of the electrode patch includes indicating the end of the duration.

In some implementations, the electrode patch is configured to be used for a duration of at least 30 days from when the electrode patch is removed from a liner of the electrode patch. Indicating the end of the predetermined lifespan of the electrode patch includes indicating the end of the duration.

In some implementations, the electrode patch is configured to be used for a cumulative duration of at least 24 hours from when the electrode patch is removed from a liner of the electrode patch. Indicating the end of the predetermined lifespan of the electrode patch includes indicating the end of the cumulative duration.

In some implementations, the electrode patch is configured to be used for a cumulative duration of at least 48 hours from when the electrode patch is removed from a liner of the electrode patch. Indicating the end of the predetermined lifespan of the electrode patch includes indicating the end of the cumulative duration.

In some implementations, the electrode patch is configured to be used for a cumulative duration of at least 3 days from when the electrode patch is removed from a liner of the electrode patch. Indicating the end of the predetermined lifespan of the electrode patch includes indicating the end of the cumulative duration.

In some implementations, the electrode patch is configured to be used for a cumulative duration of at least one week from when the electrode patch is removed from a liner of the electrode patch. Indicating the end of the predetermined lifespan of the electrode patch includes indicating the end of the cumulative duration.

In some implementations, the electrode patch is configured to be used for a cumulative duration of at least 30 days from when the electrode patch is removed from a liner of the electrode patch. Indicating the end of the predetermined lifespan of the electrode patch includes indicating the end of the cumulative duration.

In some implementations, indicating the end of the predetermined lifespan includes providing a visual indication of the end of the predetermined lifespan.

In some implementations, the visual indication is provided via a light source.

In some implementations, the visual indication is provided via a display.

In some implementations, indicating the end of the predetermined lifespan includes providing an audible indication of the end of the predetermined lifespan.

In some implementations, indicating the end of the predetermined lifespan includes providing a tactile indication of the end of the predetermined lifespan.

Implementations can include one or more of the following advantages.

In some implementations, one or more electrodes (e.g., one or more electrodes on an electrode patch) that are used in conjunction with a medical device can be monitored. For example, an indicating mechanism associated an electrode patch can indicate an end of a predetermined lifespan of the electrode patch or a remaining lifespan of the electrode patch based on the monitoring or electrode patch use time remaining or elapsed.

In some implementations, the indicating mechanism can indicate an end of a predetermined lifespan of the electrode patch and/or a remaining lifespan of the electrode patch while the electrode patch is still in its packaging or while the electrode patch is still attached to a backing/liner. In some implementations, the indicating mechanism can indicate an end of a predetermined lifespan of the electrode patch and/or a remaining lifespan of the electrode patch while the electrode patch is in use (e.g., while the electrode patch is affixed on the skin of the patient).

In some implementations, the indicating mechanism for indicating an end of a predetermined lifespan or a remaining lifespan of an electrode patch can be disposed within a controller of an external medical device that is configured for continuous, substantially continuous, long term and/or extended monitoring of the patient. In some implementations, one or more of the electrodes as described herein can be configured for providing treatment to the patient.

Other features and advantages of the examples described herein will be apparent from the drawings, detailed description, and claims.

DESCRIPTION OF DRAWINGS

The accompanying drawings are not intended to be drawn to scale. In the drawings, components that are identical or nearly identical may be represented by a like numeral. For purposes of clarity, not ever component is labeled in every drawing. In the drawings.

DETAILED DESCRIPTION

Figure 1:
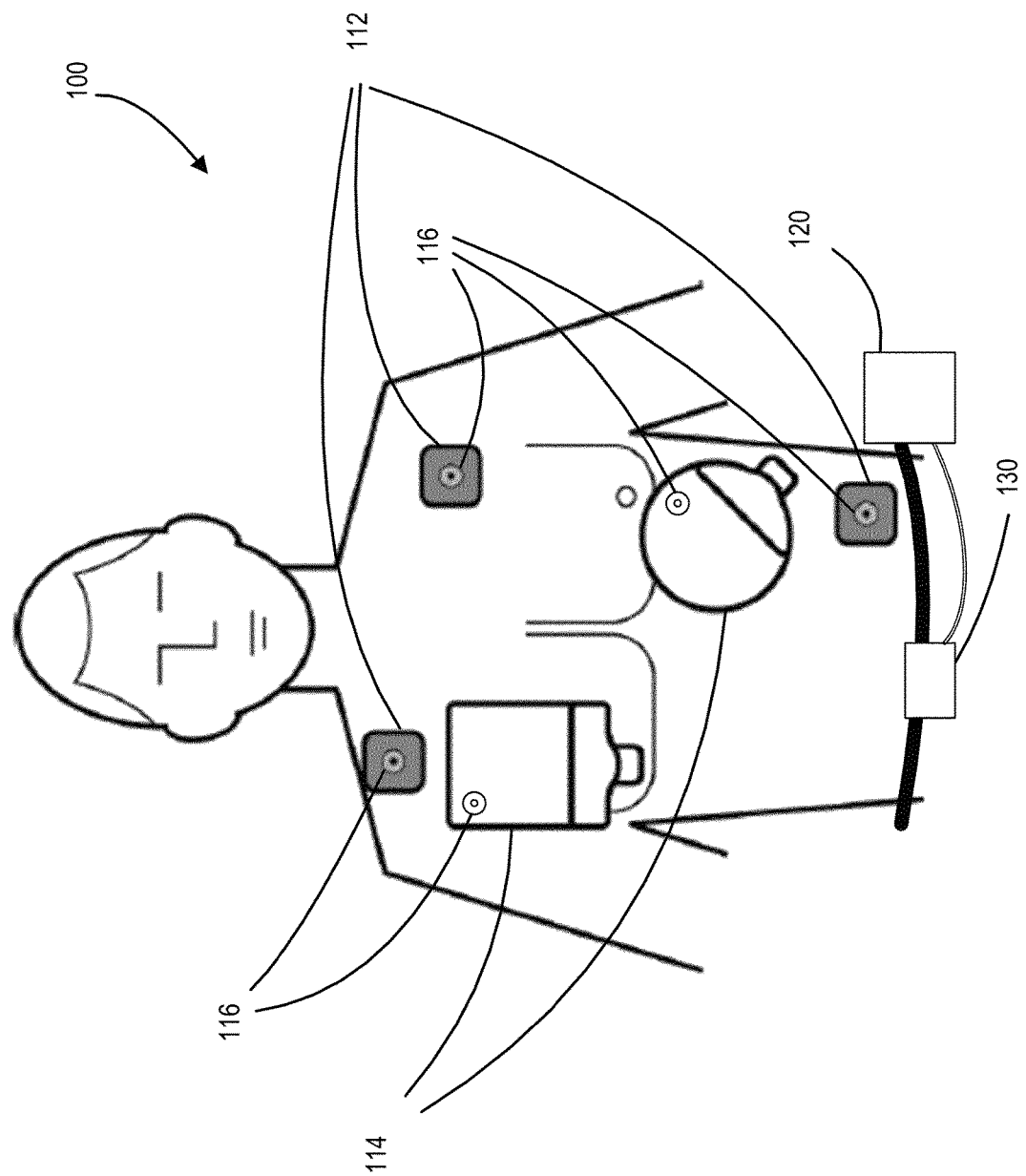
FIG. 1 is an example of a wearable medical device that includes a medical device controller.

A medical devices for use with the systems and techniques as disclosed herein can be configured to monitor one or more cardiac signals of a patient and determine whether the patient is experiencing a cardiac event. For example, the medical device can include a plurality of sensing electrodes that are disposed at various locations of the patient's body (e.g., the patient's upper body or torso) and configured to detect the cardiac signals of the patient. For example, such devices can be used as patient monitors, and more specifically, cardiac monitors in certain cardiac monitoring applications, such as Holter monitoring, mobile cardiac telemetry (MCT) and/or continuous event monitoring (CEM) applications.

In some implementations, the medical device can also be configured to determine an appropriate treatment for the patient based on the detected cardiac signals and cause one or more therapeutic pulses (e.g., defibrillating and/or pacing pulses) to be delivered to the heart of the patient. The medical device can include a plurality of therapy electrodes that are disposed at various locations of the patient's body and configured to deliver the therapeutic pulses. In some examples, the therapy electrodes can be integrated along with the sensing electrodes on a same electrode patch as described herein.

A medical device as described herein can use one or more electrodes for monitoring a patient for a cardiac arrhythmia condition such as bradycardia, ventricular tachycardia (VT) or ventricular fibrillation (VF). In addition, while the detection methods and systems described hereinafter are disclosed as detecting VT and VF, this is not to be construed as limiting the invention as other arrhythmias, such as, but not limited to, atrial arrhythmias such as premature atrial contractions (PACs), multifocal atrial tachycardia, atrial flutter, and atrial fibrillation, supraventricular tachycardia (SVT), junctional arrhythmias, tachycardia, junctional rhythm, junctional tachycardia, premature junctional contraction, and ventricular arrhythmias such as premature ventricular contractions (PVCs) and accelerated idioventricular rhythm may also be detected. In the case of treatment devices, such as pacing and/or defibrillating devices, if an arrhythmia condition is detected, the device can automatically provide a pacing, defibrillation, and/or Transcutaneous electrical nerve stimulation (TENS) pulses or shocks, as needed, to treat the condition.

An electrode patch (e.g., comprising one or more sensing electrodes, treatment electrodes, or both) may be a disposable and/or a replaceable patch that can be removed or replaced for a variety of reasons. As described above, an electrode may be part of an electrode assembly (e.g., a patch) comprising, for example, more than one electrode. For example, an electrode patch can include one or more sensing or therapy electrodes disposed within a same patch. For example, an electrode patch can include a combination of sensing and therapy electrodes within a same integrated electrode patch. For example, an electrode patch may diminish in effectiveness over time with or without use for reasons given below, and eventually some or all of the electrode patch's functionality can be lost. At such time, the electrode patch may be removed or replaced.

In some cases, the electrode patch may be removed or replaced based on a predetermined lifespan of the electrode patch as described in further detail below. In some examples, the electrode patch may be removed or replaced based on an integrity (e.g., a condition) of the electrode patch and/or one or more electrodes of the patch.

Predetermined Lifespan

An electrode patch can be removed or replaced based on a predetermined lifespan of the electrode patch (e.g., irrespective of the physical or operational condition of the patch). For example, the predetermined lifespan may be an amount of time that the patch is configured, suited, prescribed and/or recommended for wear by a patient. For example, such a predetermined lifespan may range from a few minutes, a few or several hours, days, weeks, months, and/or years. In some examples, the predetermined lifespan can be 24 hours. In some cases, the predetermined lifespan can be one week. In some examples, the predetermined lifespan can be 14 days. In certain situations, the predetermined lifespan may be 30 days or one month.

The predetermined lifespan can be measured from an occurrence of an initiating event. For instance, an initiating event may be based on detecting when the electrode patch is first affixed to the patient's skin. For instance, an initiating event may be based on detecting when a physical or operational connection between a medical device controller (e.g., controller 120, 420 described herein) and an electrode patch is established. As an example, the initiation of an operational connection between an electrode patch and the controller can be used to initiate a timing mechanism as described in further detail below.

In some cases, an initiating event may be based on detecting when the electrode patch is removed from a backing and/or liner. In an example, an initiating event may be based on detecting when the electrode patch or a portion of the electrode patch is exposed to air. In some implementations, the initiating event may be based on a user input. For example, a user may press a button, provide touchscreen input, speak and audible command, and/or otherwise indicate the user input-based initiating event. Other example initiating events are possible, including those described in further detail below. In some examples, the predetermined lifespan may be a cumulative amount of time that the electrode patch is worn by the patient (e.g., not including periods of time when the electrode patch is removed from the patient for showering or washing, or when the electrode patch is disconnected from the controller). In some cases, the predetermined lifespan can be based on a cumulative amount of time that electrical current has been running through one or more electrodes of the electrode patch.

The predetermined lifespan can be characterized through a variety of techniques for measuring use or the passage of time of use of the electrode patch. For example, a predetermined lifespan may indicate a use of the electrode patch based on a cumulative or total amount of electrical current that has been running through one or more electrodes of the electrode patch over a period of time. As such, the predetermined lifespan may be based on the total and/or cumulative use of the electrode patch for which the electrode patch may be configured for, suited, prescribed and/or recommended for a patient. For instance, the predetermined lifespan can be based on a threshold amount of total current that may be passed through one or more electrodes of the patch before the electrode patch should be removed from the patient's skin or replaced with a new electrode patch. In this manner, the predetermined lifespan can be based on actual use of the electrode patch. For example, an electrode patch that undergoes heavier than usual use may need to be removed or replaced sooner than an electrode patch that undergoes a more typical usage.

For example, the predetermined lifespan may be based on use or an amount of time elapsed since the electrode patch was first exposed to air, or use or an amount of time elapsed since the electrode patch was removed from its packaging (e.g., the electrode patch's original manufacturer packaging, separated from a liner/backing, etc.), or use or an amount of time elapsed since the electrode patch has been manufactured (e.g., an "expiration date"), among others.

For example, a patient may need to be monitored and/or potentially treated (e.g., based on a cardiac in-hospital or outpatient monitoring and/or treatment program) for a prescribed duration, e.g., 7 days. After the prescribed duration, in some cases, the patient may no longer need to be monitored. In such cases, a disposable electrode patch that has a predetermined lifespan of 7 days may be used in conjunction with the concepts described herein. Accordingly, when the electrode patch use has ended, the patch may be removed from the patient's skin. In instances in which the recommended predetermined lifespan of an electrode patch is less than that of the prescribed period of monitoring (e.g., the predetermined lifespan is about 3 days and the monitoring prescription is about 7 days), the electrode patch may be replaced by a new patch at the end of the predetermined lifespan as described in detail below.

In some examples, a surface of an electrode patch may include a conductive layer or material for allowing electrical current from one or more electrodes of the electrode patch to pass to the patient's skin. For example, the surface of an electrode of an electrode patch can include a conductive gel layer. In some implementations, the electrode patch can include an adhesive layer that affixes the electrode patch to the patient's skin and facilitates a sufficient electrical connection between the electrode patch and the patient (e.g., the impedance experienced at an electrode patch surface is within a tolerable range as described in further detail below). For example, the conductive gel layer conducts the current to the patient skin, while the adhesive layer maintains sufficient physical contact between the electrode patch and the patient's skin.

In some implementations, the conductive layer can include a conductive adhesive gel layer or material such as a conductive hydrogel-based adhesive that affixes the electrode patch to the patient's skin and facilitates the electrical connection between the electrode patch and the patient. For example, such a conductive adhesive gel layer provides both conduction of the electric current to the patient's skin as well as adhesive properties to maintain the electrical connection. Accordingly, in some implementations, the conductive adhesive gel layer may be sufficiently adhesive to the patient's skin such that the adhesive layer may be omitted. One example of such an electrode patch is described in U.S. Patent Application Publication No. US 2013/0325096, titled "LONG TERM WEAR MULTIFUNCTION BIOMEDICAL ELECTRODE," (hereinafter the "'096 patent publication") published Dec. 5, 2013, the entire contents of which are hereby incorporated by reference.

The conductive gel and/or the conductive adhesive gel can include a hydrogel material. Such hydrogel layer or material can include natural and/or synthetic polymers that are dispersed or distributed in an aqueous fluid. In some implementations, the electrode patch can include a backing/liner that also includes hydrogel material that can provide moisture to the patch's hydrogel material or receive moisture from the patch's hydrogel material.

The binding strength of the patch's adhesive (e.g., including an adhesive gel) layer can diminish over time for a variety of reasons. For example, the binding strength of the adhesive layer can diminish over time during a patient's wear as a result of the patient sweating while wearing the electrode patch. In some examples, the adhesive material may also include an appropriate amount of water content, which can gradually dry over time. The diminished binding strength as a result of these changes may cause a physical contact (and therefore an electrical connection) between the electrode patch and the patient's skin to be different than when the electrode patch was initially affixed to the patient. Thus, the amount of time that the electrode patch has been worn by the patient may be used as a basis for determining when the electrode patch should be removed or replaced.

In some examples, the electrical characteristics of the hydrogel material can vary with the hydrogel's moisture content. For example, if the hydrogel comprises an appropriate amount of water content, the conductive layer can provide a relatively low electrical impedance to the path between the conductive layer (e.g., a foil layer) and the patient's skin. However, the hydrogel's water content can diminish over time (e.g. with or without patient's use). As a result of the drying over time, an impedance as seen by the electrode patch may increase and an effectiveness of signal exchange and/or energy transfer between the patient and the electrode patch may deteriorate. In some examples, the moisture in the hydrogel may gradually dry up due to exposure to air beginning at a time when the electrode patch is removed from its packaging. Thus, the amount of time that has elapsed since the electrode patch was first exposed to air could be used as a basis for determining when the electrode patch should be removed or replaced.

In some examples, a condition of the electrode patch may be inferred based on the predetermined lifespan. For example, the predetermined lifespan may be based on a typical amount of time after which the electrode patch would be in a condition that requires removal or replacement. In some implementations, such an inference may be based on historical experimental data, e.g., data collected over the lifespan of other electrode patches undergoing real-world use or laboratory/testing use. For example, as noted above, a predetermined lifespan as described herein can be up to 24 hours. In some implementations, a predetermined lifespan as described herein can be up to 14 days (e.g., two weeks). In some implementations, the predetermined lifespan can be in the order of months or years.

As noted above, the indicating mechanism can indicate to a user, such as a patient or a caregiver (e.g., a nurse, a physician, or a physician's aide) that the electrode patch is to be removed or replaced at or substantially near an end of the patch's predetermined lifespan. For instance, the electrode patch may be configured to be worn for at least 24 hours. Accordingly, the caregiver may be prompted to remove or replace the patch at or substantially near the end of a 24 hour period beginning at a time when the electrode patch was initially affixed to the patient's skin. In various implementations, the duration of wear may be calculated without regard to whether the patch is removed from the patient's skin during the 24 hour period.

In certain implementations, a duration of electrode patch wear based on specific disposition of the patch may be used (e.g., including the times when the patch is worn by the patient and not including the times when the patch is not worn by the patient) in determining whether the patch should be removed or replaced. For example, if the patch is temporarily removed for about 30 minutes while the patient showers, then the duration for which the patch is temporarily removed may not be included in determining the total duration of patch wear for comparison with the predetermined lifespan.

In one implementation, the indicating mechanism can be configured to indicate that the patch should be removed or replaced when it detects that the patch has been removed or becomes unattached from the patient's skin. For example, when the caregiver or patient removes a patch from the patient's skin, it may be desirable to indicate to the caregiver or patient that the patch should be removed or replaced. For example, the indicating mechanism may be configured to indicate that a new patch should be used and not the patch that had become unattached. Accordingly, when the medical device controller detects that a patch has been removed from the patient's skin, the indicating mechanism can indicate that the patch should be removed or replaced. For example, as noted herein, one or more electrodes of a patch can be configured to detect that the patch is in contact with the patient's skin by detecting that the impedance experienced by the one or more electrodes is within a predetermined range (e.g., between 100-140 ohms). When a substantially higher impedance is experienced, the medical device controller can detect that the patch may have been removed from the patient's skin.

In some implementations, the patch may be configured to be worn for at least 48 hours. In some implementations, the patch may be configured to be worn for at least 3 days. In some implementations, the patch may be configured to be worn for at least 7 days. In some implementations, the patch may be configured to be worn for at least two weeks. In some implementations, the patch may be configured to be worn for at least 30 days or a month. Depending on the configured duration of wear, the predetermined lifespan can be defined accordingly. Accordingly, the caregiver may be prompted to remove or replace the patch at or substantially near the end of the predetermined lifespan. In various implementations, the duration of wear may be calculated without regard to whether the patch is removed (e.g., temporarily removed) from the patient's skin during the duration of patch use, or when the patch is disconnected (e.g., temporarily disconnected) from the controller during such use. In some implementations, a cumulative duration of wear may be considered, as described above, counting only periods when the patch is actually worn on the patient's skin or actually or operatively connected to the controller.

Integrity of the Electrode Patch

An electrode patch can be removed or replaced based on an integrity of the electrode patch, which in some examples is related to an actual condition (e.g., physical or electrical condition) of the electrode patch. The integrity of the patch can be conveyed in the form of an integrity measure that may be indicated (visually or otherwise) through the indicating mechanism described above. For example, the integrity measure may be based on a predetermined known baseline condition of the electrode patch. Various scales (numerical or otherwise) may be used, including, but not limited to an interval scale, an ordinal scale, a nominal scale, and/or a dichotomous scale (e.g., indicating either of whether the electrode patch use is acceptable or no longer acceptable). Such scales may be categorical, discrete, continuous, or based on percentages and/or ratios.

As noted above, the electrical properties of the conductive gel (e.g., both conductive gel and conductive adhesive gel) can vary with the material's moisture content. Moreover, the adhesive properties of a nonconducting adhesive layer can also vary over time for reasons described above. In these situations, an impedance value as seen by the electrode patch can increase as the moisture content of the conductive gel or the physical contact between the electrode patch and the patient's skin diminishes. In some examples, the integrity of the electrode patch can be determined based on a measure of impedance as seen by the electrode patch and the medical device controller. As such, a measurement of the integrity of the electrode patch may provide an accurate indication of the electrode patch's current utility.

The integrity of an electrode patch can be a signal integrity or a physical integrity. For example, signal integrity may represent a characteristic of an electrical signal measured at or in association with the electrode patch. As such, the signal integrity can represent a condition of the electrode patch-skin interface. For example, physical integrity may represent a physical condition and/or state of one or more electrodes of the electrode patch. While the two types of integrity are distinct, they can be related; for example, the signal integrity can be indicative of the physical integrity.

In some implementations, signal integrity can be determined based on an impedance of the electrical path between the electrode patch and the patient (e.g., based on the electrode patch-skin interface). In some examples, when a new electrode patch that is newly attached to the medical device is used, the path between the electrode patch and the patient exhibits a relatively low impedance, and thus has a relatively good signal integrity. After the electrode patch has been in use for a period of time, the impedance may begin to increase. For example, as the conductive adhesive begins to degrade and/or dry up, the electrode patch may experience increased impedance.

In some examples, physical integrity is associated with a physical condition relating to a geometry of the electrode patch. When an electrode patch becomes physically compromised, it may be appropriate to remove or replace the electrode patch. For example, the electrode patch may warp and/or begin to peel, and/or one or more voids may form within the adhesive layer. In some examples, the physical integrity of the electrode patch may be associated with a state of the patch, e.g., the electrode patch may become wet, get exposed to corrosive fluids (e.g., sweat, spilled liquids such as beverages, etc.), become damaged or ruptured due to contact with sharp edges, etc. In some implementations, the physical integrity of the electrode patch is determined based on one or more impedance measurements of the electrical path between the electrode patch and the patient. For example, if an electrode patch experiences relatively high impedance, it may indicate that the electrode patch is not in good contact with the patient's skin. Thus, in some cases, while the determination of whether the electrode patch should be removed or replaced is based on the physical integrity of the electrode patch, the determination may be made indirectly based on the impedance as seen by the electrode patch.

Example Medical Devices

The medical devices disclosed herein can be configured to indicate when an electrode patch should be removed or replaced based on a predetermined lifespan of the electrode patch and/or an integrity of an electrode patch.

In some implementations, the medical device is an external medical device (e.g., in contrast to internal or implanted devices, such as implantable medical devices). For example, the external medical device can be a cardiac monitoring and/or automated pacing device or defibrillators, such as an in-facility continuous monitoring defibrillator (e.g., for patients that are confined to a limited space within a facility, such as, within a hospital environment, to a patient's room) or outpatient wearable defibrillators. The medical device can be configured to monitor a patient for one or more cardiac arrhythmia conditions such as bradycardia, ventricular tachycardia (VT) ventricular fibrillation (VF), and/or supraventricular tachycardia. In some implementations, if an arrhythmia condition is detected, the device can automatically provide a pacing or defibrillation pulse or shock to treat the condition.

In some implementations, an external medical device can be an automated cardiac monitor or defibrillator that can be used in certain specialized conditions and/or environments such as in combat zones or within emergency vehicles. The medical device can be configured for immediate (or substantially immediate) use in a life-saving emergency. In some examples, medical device can be pacing-enabled (e.g., capable of providing therapeutic pacing pulses to the patient). For example, the external medical device can be an automated external defibrillator (AED). Such AEDs are available from ZOLL® Medical Corporation of Chelmsford, Mass.

In some implementations, the external medical device is an ambulatory device (e.g., a device that is capable of and designed for moving with the patient as the patient goes about his or her daily routine). In some examples, the external medical device can be configured as a wearable defibrillator, such as the LifeVest® wearable cardioverter defibrillator available from ZOLL® Medical Corporation of Chelmsford, Mass.

The devices as described herein may be capable of continuous, substantially continuous, long-term and/or extended use or wear by, or attachment or connection to a patient.

For example, devices as described herein may be capable of being used or worn by, or attached or connected to a patient, without substantial interruption for a predetermined period of time. In some examples, such devices may be capable of being used or worn by, or attached or connected to a patient for example, up to hours or beyond (e.g., weeks, months, or years).

In some implementations, such devices may be removed for a period of time before use, wear, attachment, or connection to the patient is resumed, e.g., to change batteries, to change the garment, and/or to take a shower, without departing from the scope of the examples described herein.

The devices as described herein may be capable of continuous, substantially continuous, long-term and/or extended monitoring of a patient.

For example, devices as described herein may be capable of providing cardiac monitoring without substantial interruption for a predetermined period of time. In some examples, such devices may be capable of continuously or substantially continuously monitoring a patient for cardiac-related information (e.g., ECG information, arrhythmia information, heart sounds, etc.) and/or non-cardiac information (e.g., blood oxygen, the patient's temperature, glucose levels, and/or lung sounds), for example, up to hours or beyond (e.g., weeks, months, or years).

In some implementations, such devices may be powered down for a period of time before monitoring is resumed, e.g., to change batteries, to change the garment, and/or to take a shower, without departing from the scope of the examples described herein.

In some instances, the devices may carry out its monitoring in periodic or aperiodic time intervals or times. For example, the monitoring during intervals or times can be triggered by a user action or another event. For example, one or more durations between the periodic or aperiodic intervals or times can be user-configurable.

In some implementations, the medical device as described herein can be a hospital based medical device including, for example, a cardiac monitoring device, a defibrillator and/or pacing device. For example, such a hospital based device can include a defibrillator and/or pacing device configured for continuous or substantially continuous use, wear, connection, attachment, or monitoring to/of a patient in a hospital environment. The hospital based device can include a plurality of therapy and sensing electrodes that are attached to the patient's skin. In some examples, the sensing and/or therapy electrodes are disposable adhesive electrodes. In some implementations, the electrodes are affixed to an electrode assembly (e.g., a patch), which can then be adhesively attached to the patient's skin. The sensing and/or therapy electrodes can be attached to the patient's skin at particular locations as prescribed by a trained professional.

In some implementations, the medical device as described herein can be configured to monitor a patient presenting with syncope (e.g., by analyzing the patient's cardiac activity for aberrant patterns that can indicate abnormal physiological function). In some examples, aberrant patterns may occur prior to, during, or after the onset of syncope symptoms. For example, the short-term outpatient defibrillator can include a plurality of electrodes and/or an electrode assembly (e.g., a patch) that can be adhesively attached to the patient's skin. The patient may remove or replace the electrodes and/or patches as prescribed.

For example, the medical device can include a user interface for interacting with the medical device. The device can include one or more input mechanisms (e.g., buttons) that the patient can interact with in order to respond to a treatment alert. In some examples, the medical device issues a treatment alert before providing a treatment pulse, and if the patient does not respond to the treatment alert (e.g., by holding down one or more response buttons), the device can deliver the treatment pulse to restore normal heart rhythm.

Example Wearable Medical Device

FIG. 1 illustrates an example wearable medical device 100. The wearable medical device 100 includes a plurality of sensing electrodes 112 that can be disposed at various positions about the patient's body. The sensing electrodes 112 are electrically coupled (coupling not shown in the figure) to a medical device controller 120 through a connection pod 130. In some implementations, some of the components of the wearable medical device 100 are affixed to a garment (e.g., a belt) that can be worn on the patient's torso. For example, as shown in FIG. 1, the controller 120 and the connection pod 130 are mounted on the patient's belt. The sensing electrodes 112 are configured to monitor the cardiac function of the patient (e.g., by monitoring one or more cardiac signals of the patient). While FIG. 1 shows three sensing electrodes 112, additional sensing electrodes may be provided, and the plurality of sensing electrodes 112 may be disposed at various locations about the patient's body. In some examples, as noted above, more than one sensing electrodes 112 can be disposed within a single sensing electrode patch.

The wearable medical device 100 can also optionally include a plurality of therapy electrodes 114 that are electrically coupled (coupling not shown in the figure) to the medical device controller 120 through the connection pod 130. The therapy electrodes 114 are configured to deliver one or more therapeutic defibrillating pulses to the heart of the patient if it is determined that such treatment is warranted. The connection pod 130 may include electronic circuitry and one or more sensors (e.g., a motion sensor, an accelerometer, etc.) that are configured to monitor patient activity. In some implementations, the wearable medical device 100 may be a monitoring only device that omits the therapy delivery capabilities and associated components (e.g., the therapy electrodes 114). In some implementations, various treatment components may be packaged into various modules that can be attached or removed from the wearable medical device 100 as needed.

One or more of the sensing electrodes 112 and/or the therapy electrodes 114 include an indicating mechanism such as an electrode use indicator 116. The electrode use indicator 116 is configured to indicate information related to a lifespan of the respective electrode patch or information related to an integrity of the electrode patch, as described in more detail below. As noted above, sensing electrodes 112 can be included in a sensing electrode patch comprising two or more sensing electrodes 112 (not shown), therapy electrodes can be included in a therapy electrode patch comprising two or more therapy electrodes 114 (not shown), or at least one sensing and at least one therapy electrode of the sensing electrodes 112 and therapy electrodes 114 can be integrated into a single electrode patch. In such electrode patch implementations, the electrode use indicator 116 can be configured to indicate information related to the lifespan of the corresponding electrode patch or information related to an integrity of the electrode patch.

For example, the electrode use indicator 116 can include a light source (e.g., an LED) that can emit light in various colors. In some implementations, the color of the light can indicate an end of a predetermined lifespan of the electrode. For example, the light source can emit a red light when the predetermined lifespan of the electrode patch has ended (e.g., after a particular amount of time has elapsed since the electrode patch was first exposed to air). In some examples, the electrode use indicator 116 can be powered by a separate power source other than the battery of the controller 120. For example, the separate power source can include a battery such as a flat or button type battery (e.g., CR2032, LR44, etc.). In some examples, the electrode use indicator 116 can be powered from the battery of the controller 120.

The controller 120 includes response buttons and a touch screen that the patient can interact with in order to communicate with the medical device 100. The controller 120 also includes a speaker for communicating information to the patient and/or a bystander. In some examples, when the controller 120 determines that the patient is experiencing cardiac arrhythmia, the speaker can issue an audible alarm to alert the patient and bystanders to the patient's medical condition. In some examples, the controller 120 can instruct the patient to press and hold one or both of the response buttons on the medical device controller 120 to indicate that the patient is conscious, thereby instructing the medical device controller 120 to withhold the delivery of one or more therapeutic defibrillating pulses. If the patient does not respond to an instruction from the controller 120, the medical device 100 may determine that the patient is unconscious and proceed with the treatment sequence, culminating in the delivery of one or more defibrillating pulses to the heart of the patient.

Figure 2B:
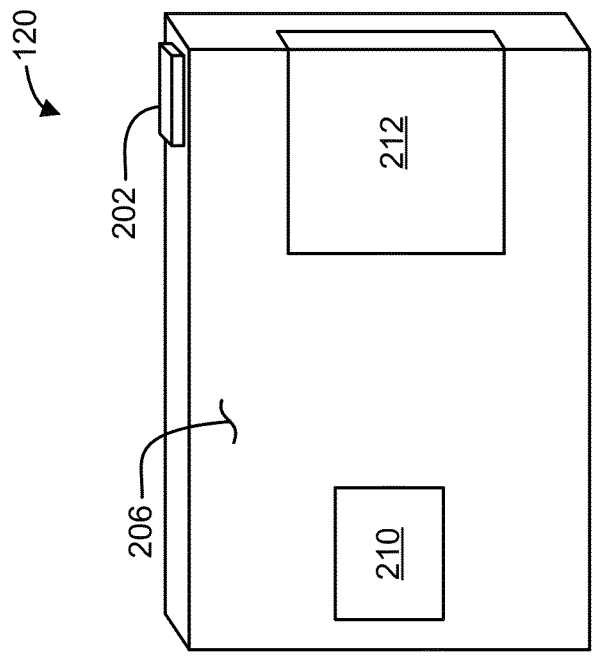
FIGS. 2A-2B show an example of the medical device controller of FIG. 1.
Figure 2A:
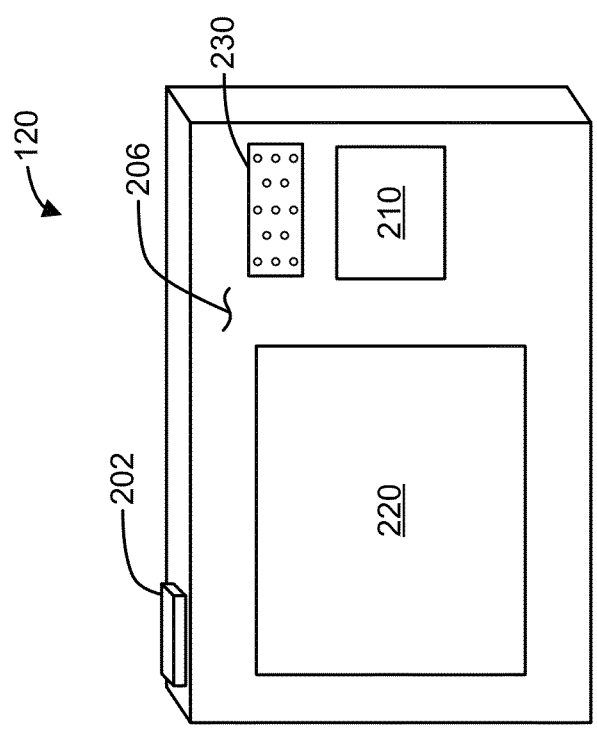

FIGS. 2A (front view) and 2B (rear view) show an example of the medical device controller 120. The controller 120 may be powered by a rechargeable battery 212. The rechargeable battery 212 may be removable from a housing 206 of the medical device controller 120 to enable a patient and/or caregiver to swap a depleted (or near depleted) battery 212 for a charged battery. The controller 120 includes a user interface such as a touch screen 220 that can provide information to the patient, caregiver, and/or bystanders. The patient and/or caregiver can interact with the touch screen 220 to control the medical device 100. The controller 120 also includes a speaker 230 for communicating information to the patient, caregiver, and/or the bystander. The controller 120 includes one or more response buttons 210. In some examples, when the controller 120 determines that the patient is experiencing cardiac arrhythmia, the speaker 230 can issue an audible alarm to alert the patient and bystanders to the patient's medical condition. In some examples, the controller 120 can instruct the patient to press and hold one or both of the response buttons 210 to indicate that the patient is conscious, thereby instructing the medical device controller 120 to withhold the delivery of therapeutic defibrillating pulses. If the patient does not respond to an instruction from the controller 120, the medical device 100 may determine that the patient is unconscious and proceed with the treatment sequence, culminating in the delivery of one or more defibrillating pulses to the heart of the patient. The medical device controller 120 may further include a port 202 to connect removable sensing electrodes (e.g., ECG sensing electrodes 112) and/or therapeutic electrodes (e.g., therapy electrodes 114), and/or electrode patches, to the medical device controller 120.

Figure 3:
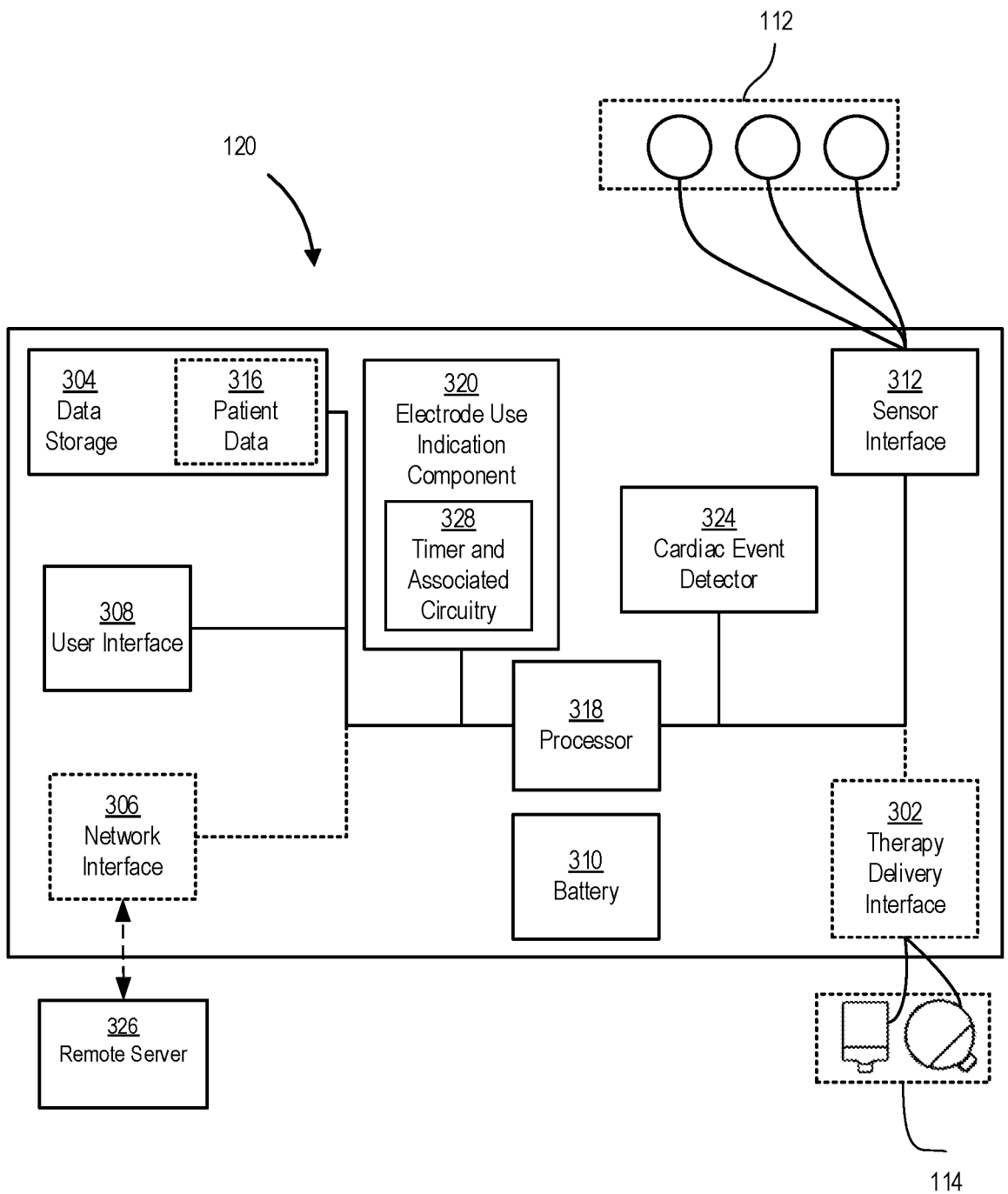
FIG. 3 is a functional schematic of the medical device controller of FIGS. 1 and 2A-2B.

FIG. 3 shows a schematic of an example of the medical device controller 120 of FIGS. 1 and 2A-2B. The controller 120 includes a processor 318, an electrode use indication component 320, a cardiac event detector 324, an electrode system, e.g., a sensor interface 312, and an optional therapy delivery interface 302, data storage 304 (which may include patient data 316), an optional network interface 306, a user interface 308 (e.g., including the touch screen 220 shown in FIGS. 2A-2B), and a battery 310. The electrode system comprising the sensor interface 312 and/or the therapy delivery interface 302 is configured to communicate signals to and/or from one or more electrodes 112, 114. For example, the sensor interface 312 is coupled to the sensing electrodes 112, and the therapy delivery interface 302 (if included) is coupled to the therapy or treatment electrodes 114. The sensor interface 312 and the therapy delivery interface 302 implement a variety of coupling and communication techniques for facilitating the exchange of data between the electrodes 112, 114 and the controller 120.

Figure 6:
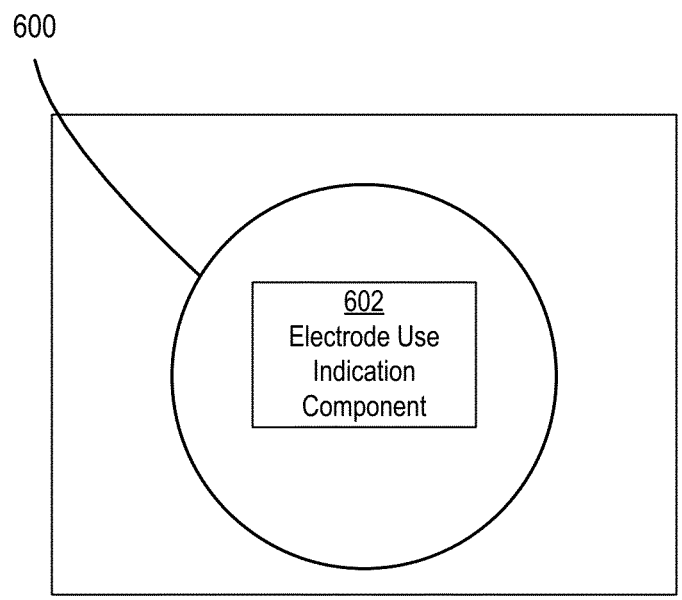
FIG. 6 shows an example of an electrode patch that includes an electrode use indication component.

In some implementations, the electrode use indication component 320 may be fully contained within the electrode (e.g., on either or both the sensing electrodes 112 and/or therapy electrodes 114, or on an electrode patch), as shown in FIG. 6. For example, the electrode use indication component 320 may be included on an electrode patch as circuitry along with an indicating mechanism such as an LED light controlled through the circuitry.

In some examples, the electrode use indicator disposed on the electrode patch may contain wireless communications circuitry (e.g., a Bluetooth® wireless module) that can wirelessly communicate with the electrode use indication component 320.

In some implementations, one or more functions of the electrode use indication component 320 can be performed by circuitry contained within the controller 120 and other one or more functions of the electrode use indication component 320 can be performed by circuitry disposed in the electrode.

In some implementations, the processor 318 can perform a series of instructions that control the operation of the other components of the controller 120. The cardiac event detector 324 is configured to monitor the cardiac activity of the patient and identify cardiac events experienced by the patient based on received cardiac signals. In some examples, the cardiac event detector 324 can access patient templates (e.g., which may be stored in the data storage 304 as patient data 316) that can assist the cardiac event detector 324 in identifying cardiac events experienced by the particular patient. In some examples, the network interface 306 can facilitate the communication of information between the controller 120 and one or more other devices or entities over a communications network. In some examples, the network interface 306 is configured to communicate with a server (e.g., a remote server 326). A caregiver can access the data from the remote server 326 to access information related to the patient.

The electrode use indication component 320 is configured to monitor a use of one or more electrode patches coupled to the controller 120 and determine information related to lifespans and/or integrity of the patches. The electrode use indication component 320 is also configured to control the electrode use indicators 116 based on the determined electrode patch information, as described in more detail below. The electrode use indication component 320 may display relevant electrode patch use, lifespan, and/or integrity information via the user interface 308 of the controller 120.

Example Monitoring Medical Device

While the controller 120 of FIGS. 1-3 has been described as being part of the wearable medical device 100 of FIG. 1, a similar controller can also be part of other medical devices (e.g., other wearable medical devices).

Figure 4:
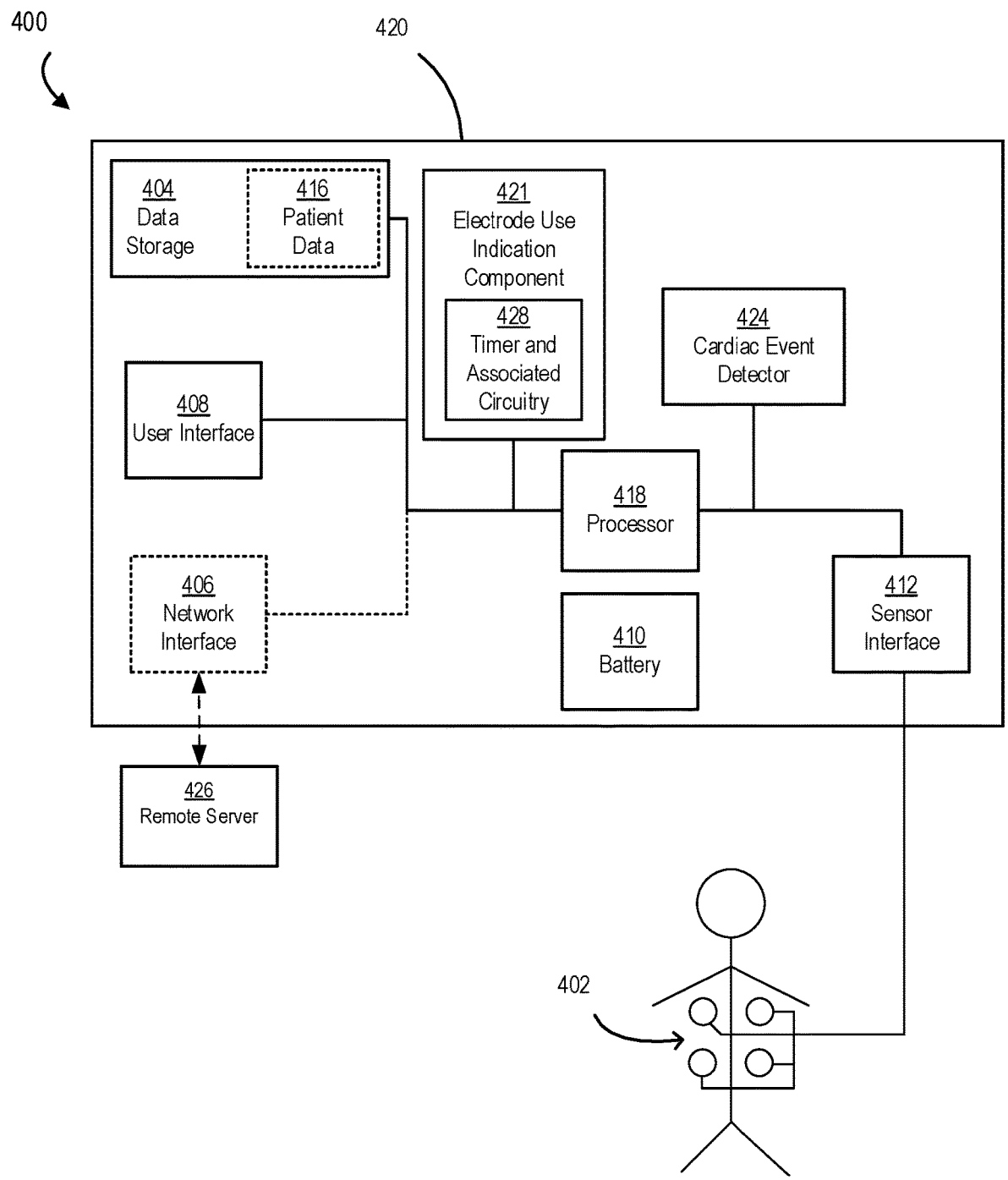
FIG. 4 is a functional schematic of an example of a cardiac monitor.

As discussed above, in some implementations, the medical device can be a dedicated patient monitoring device that is configured monitor to one or more patient conditions and/or physiological parameters, for example, cardiac activity of a patient in Holter, mobile cardiac telemetry (MCT)

and/or continuous event monitoring (CEM) applications. In some examples, the patient monitoring device may, in addition to cardiac monitoring, perform monitoring of other relevant patient parameters (e.g., weight, glucose levels, blood oxygen levels, and/or blood pressure). FIG. 4 illustrates an example wearable monitoring medical device, e.g., a cardiac monitor 400. In some implementations, the cardiac monitor 400 is capable of and designed for being worn by a patient who is at risk of developing cardiac problems. In an example, such a patient may not yet meet criteria to be outfitted with a medical device that includes a treatment component (e.g., a defibrillator). Thus, the cardiac monitor 400 may be prescribed so that continuous and/or event-based data can be sent from the cardiac monitor 400 to a server (e.g., the remote server 426). A caregiver can access the data from the remote server 426 and determine whether the patient is experiencing or has experienced a cardiac problem. In some implementations, after determining that the patient is experiencing a cardiac problem, the caregiver may instruct the patient to cease wearing the cardiac monitor 400 and instead wear a medical device with treatment capabilities.

The cardiac monitor 400 includes the medical device controller 420 (e.g., similar to controller 120 of FIGS. 1-3 without, for example, the treatment/therapy elements as shown). Accordingly, the medical device controller 420 used in conjunction with a cardiac monitor 400 operates in a similar fashion as described above. The cardiac monitor includes the plurality of sensing electrodes 402. In some examples, the sensing electrodes 402 can be an integral part of a housing structure of the cardiac monitor 400.

The controller 420 includes a processor 418, an electrode use indication component 320, a cardiac event detector 424, an electrode system, e.g., a sensor interface 412, data storage 404 (which may include patient data 416), an optional network interface 406, a user interface 408 (e.g., including a touch screen 220 as shown in FIGS. 2A-2B), and a battery 410. The electrode system comprising the sensor interface 412 is configured to communicate signals to and/or from one or more electrodes 402. The sensor interface 412 can be configured to implement a variety of coupling and communication techniques for facilitating the exchange of data between the electrodes 402 and the controller 420.

In some implementations, the patient can interact with the user interface 408 to identify a patient symptom. The user interface 408 may include a drop down menu or check list that allows the patient to select a particular symptom from a list of alternatives. Options for patient systems can include one or more of: feeling a skipped beat, shortness of breath, light headedness, racing heart rate, fatigue, fainting, chest discomfort, weakness, dizziness, and/or giddiness. In addition, the patient can select a level of activity (e.g., light activity, moderate activity, rigorous activity, etc.) that he or she was performing when the symptom occurred. In some implementations, in response to the selection by the patient, the cardiac event detector 424 can cause a portion of patient physiological information (e.g., in the form of a cardiac signal) to be captured for a length of time that is based on when the symptom was experienced. For example, the cardiac event detector 424 can cause a portion of an ECG signal of the patient to be captured. The portion of the ECG signal is sometimes referred to herein as an ECG strip. In some implementations, the cardiac monitor 400 can continuously record ECG data, and at the same time also identify and record one or more ECG strips relating to one or more events of interest (e.g., patient-reported symptoms, events detected by the cardiac event detector 424, etc.). As such, if a caregiver wishes to view ECG data for a period of time prior to or after the recorded ECG strip relating to an event of interest, such data is available for review from the continuously-recorded ECG data.

The electrode use indication component 421 operates in a similar fashion as electrode use indication component 320 described herein in connection with FIG. 3. For example, the electrode use indication component 421 is configured to monitor a use of one or more electrode patches used in association with the controller 420 and determine information related to lifespans and/or integrity of the patches. The electrode use indication component 421 is also configured to control electrode use indicators based on the determined electrode patch information, as described in more detail below. The electrode use indication component 421 may display relevant electrode patch use, lifespan, and/or integrity information via the user interface 408 of the controller 420. For example, the electrode use indication component 421 is configured to determine information related to a lifespan and/or information related to an integrity of the sensing electrodes 402. The electrode use indication component 421 is also configured to control the electrode use indicators based on the determined electrode patch information of the respective electrode. As described above, in some implementations, the electrode use indication component 421 may be fully contained within the sensing electrodes used in conjunction with the cardiac monitor 400. For example, the electrode use indication component 421 may be included on a sensing electrode as circuitry along with an electrode use indicator such as LED lights controlled through the circuitry.

As described above, the electrodes and/or electrode patches described herein can be used for sensing a variety of patient signals and/or conditions, treatment of such patient conditions, or both. For example, the electrodes and/or electrode patches described herein can include sensors capable of measuring and/or be used for receiving and/or monitoring cardiac and non-cardiac patient signals, such as, ECG data (e.g., continuous ECG data), heart sounds data, tissue fluid measurements/data, lung fluid measurements/data, respiration measurements/data, chest movement measurements/data, Cardiopulmonary resuscitation (CPR) measurements/data, premature ventricular contraction (PVC) measurements/data, heart rate information, patient symptom data (e.g., patient-reported symptoms and/or automatically detected patient symptom information), patient thoracic impedance measurements/data, pectoral impedance measurements/data, blood pressure, patient movement and activity measurements/data, one or more patient skin conditions, temperature, blood glucose levels, and blood oxygen levels. In various implementations, the electrodes and/or patches described herein are capable of detecting and/or sensing a variety of other patient signals, conditions and/or related measurements/data.

Electrode Use Indication Component—Predetermined Lifespan

As described above, it may be desirable for an electrode patch to be removed or replaced based on a predetermined lifespan of the electrode patch. For example, the electrode use indication component 320, 421 is configured to monitor use of one or more electrode patches and indicate when the one or more patches should be removed or replaced. Such electrode patch usage information can include whether an end of a predetermined lifespan of the electrode patch has been reached.

As noted above, the predetermined lifespan may be based on (and in some cases, may be an approximation of) a time after which the electrode patch would typically have a condition that requires removal or replacement. Thus, an electrode patch that is removed or replaced based on its predetermined lifespan may be replaced irrespective of the actual condition of the electrode patch. For instance, the electrode use indication component 320, 421 can be configured to receive user input specifying, for a corresponding electrode patch, the predetermined lifespan. Such user input may be provided via the user interface 308, 408 during an initial configuration of the controller 120, 420. In some cases, the predetermined lifespan for an electrode patch may be set by default in the controller 120, 420.

In some implementations, the controller 120, 420 can be configured to monitor the electrode patch and indicate whether the patch is to be removed or replaced based on an integrity (e.g., a condition) of the patch, as described in more detail below. For example, in some implementations, a measurement of an impedance of the electrical path between the electrode patch and the patient may indicate that the electrode patch is damaged, deteriorated, and/or degraded, and/or no longer making an appropriate level of contact with the patient's skin. Sensing electrodes that experiences relatively high (e.g., higher-than-desired) impedance may experience signal degradation due to increased noise, thereby hinder the medical device's ability to identify and analyze the signals. Therapy electrodes that experience relatively high impedances may not be optimal for, e.g., supplying sufficient electrical energy for an effective therapeutic pulse to the patient. Thus, it may be desirable for the electrode use indication component 320, 421 to indicate that the patch is to be removed or replaced in such circumstances.

The criteria for determining an appropriate time for replacing an electrode patch may also depend on the physical characteristics of the particular electrode patch. For example, an electrode patch that includes a hydrogel layer may have a certain predetermined lifespan that is selected based on estimations relating to loss of moisture content of the hydrogel layer over time. For example, as the hydrogel dries over time, the impedance of the electrical path between the electrode patch and the patient may increase, thereby diminishing an efficacy of the electrode patch.

The effectiveness (e.g., the impedance-reducing ability or the adhesive strength) of the conductive gel can diminish for a variety of reasons. In some implementations, the water content in the conductive gel may begin to gradually dry up starting from the time when the electrode patch was initially removed from its packaging or removed from a lining/backing. In some implementations, the water content in the conductive gel may gradually dry up while the electrode patch is in its packaging and/or while the electrode patch is still attached to the lining/backing.

In some examples, when an initiating event occurs, a timer (e.g., based on a timing mechanism comprising circuitry configured to keep track of time) begins to run. In an implementation, such an initiating event can be based on detecting a physical or operative connection between an electrode patch and the controller 120, 420. While electric/electronic circuitry is described for the implementation of this example, other mechanisms for tracking the passage of time can be used as described herein. For instance, such mechanisms can use other technologies and/or materials such as color-changing technologies and materials, chemically reactive technologies and materials, and the like as discussed in further detail below.

For example, the timer can be initiated by user action (e.g., by activating a button or other input mechanism) to indicate that the electrode patch timer should begin to run (e.g., when the electrode patch has been affixed to the patient's skin). In some instances, the timer can be automatically initiated when the electrode patch is affixed to the patient's skin. For example, a typical patient's thoracic impedance is within a range of 20 Ohms to about 250 Ohms. Accordingly, when the electrode patch is still affixed to its liner and/or backing, an impedance of the electrode patch may be of an amount that indicates that the electrode patch is not attached to the patient. For example, if the electrode patch is still attached to a liner, the impedance may be in excess of 50 kOhms, or more. In some implementations, when the electrode patch impedance goes from a high value (e.g., a range of kOhms or more) to be within a range of 20-250 Ohms, the timer can be initiated to indicate that the electrode patch has been affixed to the patient's skin.

For example, the timer and associated circuitry 328, 428 may be in the controller (e.g., controller 120, 420) as part of the electrode use indication component 320, 421. As such, a remaining or elapsed amount of time in the predetermined lifespan can be displayed via an indicating mechanism such as a user interface of the monitor (e.g., user interface 308 of FIG. 3 or user interface 408 of FIG. 4), one or more LEDs, or other such mechanisms. In some implementations, the timer and associated circuitry 328, 428 may be disposed as the electrode use indication component 320, 421 within the electrode patch. Further, an indicating mechanism may be disposed on the electrode patch (e.g., a surface of the electrode patch) for visually indicating to a user the remaining or elapsed amount of time. In some implementations, the indicating mechanism may provide audible (e.g., via a speaker device) or tactile alerts (e.g., via a vibration alerting device) and/or reminders for indicating to the user the remaining or elapsed amount of time.

Once the timer has been running for the predetermined lifespan set in the controller 120, 420 (e.g., two weeks), the controller 120, 420 can indicate that the electrode patch should be removed or replaced. In some implementations, once the timer has started to run, it may continue to run regardless of changes in the underlying use of the electrode patch until it has reached an end of the predetermined lifespan, such that the timer may indicate through the indicating mechanism that the electrode patch should be removed or replaced. In some implementations, the timer can be paused and/or suspended when the electrode patch is removed (e.g., temporarily removed) from the patient's skin, e.g., to wash or bathe the patient. In some examples, the timer can be manually paused by a caregiver or a patient. Accordingly, a button or other input mechanism or user interface element may be disposed on the electrode patch or the controller (e.g., controller 120, 420) and be configured to receive input from a user to pause or resume the timer.

For example, the timing mechanism may detect an underlying change in the electrode patch and automatically pause or resume the timer. For example, when the electrode patch experiences a high impedance (e.g., a range of kOhms or more) because of removal from the patient's skin, the timer can be paused or suspended. When the electrode patch impedance is returned to within an expected patient impedance range, the timer can be resumed.

In another example, when the controller 120, 420 detects that a physical or operational connection with the electrode patch has been interrupted, the timer can be paused or suspended. When the connection is restored, the timer can be resumed. In some situations, when the electrode patch is affixed to the patient but disconnected from the medical device controller 120, 420 the electrode use indicator component 320, 421 can cause the timer to continue tracking the passage of time.

The electrode use indication component 320, 421 is configured to determine when an end of the predetermined lifespan of the electrode patch has been reached. In some implementations, the electrode use indication component 320, 421 monitors the electrode patch and makes the determination based on the monitoring. The electrode use indication component 320, 421 can receive information related to the predetermined lifespans of one or more patches. In some examples, the predetermined lifespans can be manually set (e.g., input by a caregiver), provided by a manufacturer of the electrode patch, and/or provided according to a medical standard. In some examples, the predetermined lifespans can be retrieved from a database at a remote location (e.g., over a wired or wireless connection between the medical device and a computer system at the remote location).

As noted above, the timing mechanism may be part of the electrode use indication component 320, 421 or may be a separate component. In some implementations, the timing mechanism can be circuitry configured to keep track of time, or software executed by the processor to keep track of time, among others. In some implementations, the timing mechanism may track the passage of time through clock circuitry or other mechanism known to those skilled in the art. For example, such clock circuitry may comprise a local oscillator circuit (e.g., incorporating a crystal oscillator). In some examples, the clock circuitry may be synchronized based on a remote time server (e.g., located on a LAN or Internet-based network to which the medical device may be connected), and/or standardized time keeping signals (such as GPS signals).

As described above, the timing mechanism can be initiated upon the occurrence of one or more initiating events such as when the patch is separated from a backing/liner or exposure of the patch or a portion of the patch to air or ambient light. For instance, in one implementation, the electrode use indication component 320, 421 can be configured to communicate with one or more sensors (e.g., oxygen sensors), which may be located on the electrode patch. For example, the sensor may be located on an adhesive side of the electrode patch and covered by the electrode patch's liner and/or backing. When the oxygen sensor first senses oxygen in an amount beyond a particular threshold, the electrode use indication component 320, 421 can infer that the electrode patch has been exposed to air and instruct the timing mechanism to run. In some implementations, a photosensitive resistance sensor may be disposed on the adhesive side of the electrode patch and covered by the electrode patch's liner and/or backing. When the photosensitive sensor first senses ambient light in an amount beyond a particular threshold, its resistance may vary in accordance with the intensity of the ambient light. Through changes in current flow affected by the changes in resistance, the electrode use indication component 320, 421 can infer that the electrode patch has been removed from its liner and/or backing and instruct the timing mechanism to run. When the timer reaches an amount of time equal to the predetermined lifespan of an electrode patch, the electrode use indication component 320, 421 can trigger an indication that the electrode patch should be removed or replaced.

In some implementations, the electrode use indication component 320, 421 is in communication with the electrode patch and is configured to determine when the electrode patch is being worn by the patient and/or when electrical current is running through the electrode patch. While the electrode patch is being worn and/or electrical current is running through the electrode patch, the electrode use indication component 320, 421 can instruct the timer to run.

In some implementations, as long as current is passing through the electrode patch (and, e.g., for a predetermined amount of time thereafter), the timer may run. When the current is stopped or suspended, the timer may be paused. And when the current is resumed, the timer may continue to run. When the timer reaches an amount of time equal to the predetermined lifespan of the electrode patch, the electrode use indication component 320, 421 can trigger an indication that the electrode patch should be removed or replaced.

While a timer for tracking a passage of time is described above, other techniques for detecting electrode patch use relative to the predetermined lifespan can be employed. For example, the electrode use indication component 320, 421 may track a cumulative amount of current passed through the electrode patch and compare the cumulative amount of current with a predetermined lifespan expressed as a cumulative current threshold.

Example Electrode Patch Use Indicators—Predetermined Lifespan

As mentioned above, one or more of the electrode patches can include an electrode use indicator (e.g., 116 of FIG. 1) that is configured to communicate with the electrode use indication component 320, 421 and indicate information related to the predetermined lifespan or integrity of the electrode patch. The electrode use indication component 320, 421 can instruct an electrode use indicator to provide an indication when the predetermined lifespan of the electrode patch has been reached. In some implementations, the electrode use indicator does not communicate with an electrode use indicator component, and instead independently provides an indication when the predetermined lifespan of the electrode patch has been reached.

Figure 5A:
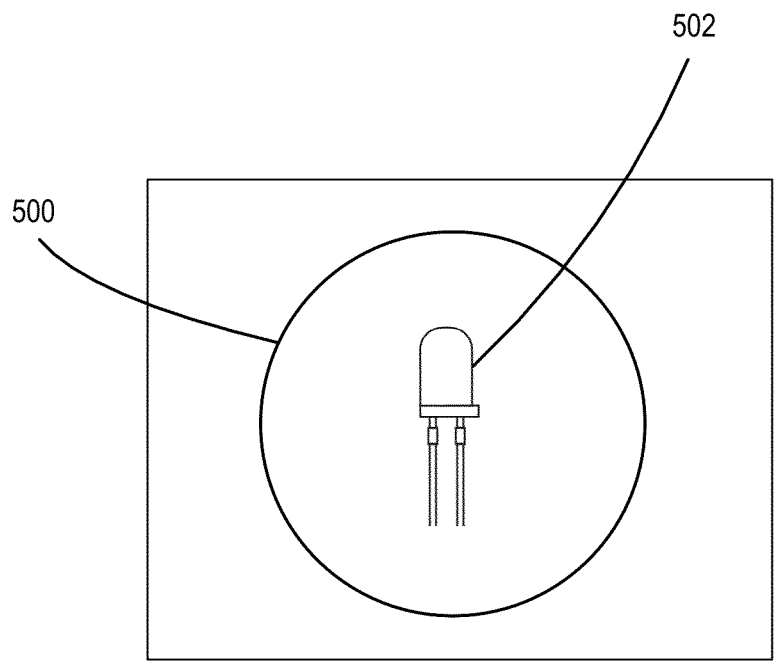
FIGS. 5A-5D shows electrodes with example electrode use indicators.

FIG. 5A shows an electrode patch 500 that is affixed to a liner and that includes an example electrode use indicator. In this example, the electrode use indicator is a light source 502 (e.g., an LED) that can emit light in various colors. For example, the light source 504 can emit a red light when the predetermined lifespan of the electrode patch has been reached (e.g., when the end of a predetermined wear time has been reached). In such cases, the red light can remain lit until the electrode patch is removed or replaced. In some implementations, the light source 504 emits a green light or be unlit when the predetermined lifespan of the electrode patch has not yet been reached. In some implementations, the light source 504 emits an orange light when the electrode use information indicates that the electrode patch use is within a predefined range of the predetermined lifespan of the electrode patch (e.g., 80% of the predetermined lifespan). In some implementations, the light source 504 emits a yellow light or no light when it is unknown whether the predetermined lifespan of the electrode patch has been reached. The electrode use indicator may indicate the various statuses of electrode patch use and/or remaining lifespan through other ways. For example, instead of different colors, the light source 504 may flash with a rate that changes in accordance with a remaining lifespan of the electrode patch (e.g., faster flashing rate indicates that the use is nearing the predetermined lifespan, while a steady light indicates that the predetermined lifespan has been reached). For example, the light source 504 may include a plurality of LEDs and/or use a combination of flashing and colors to indicate the changing electrode patch use status. For example, the colors of the light source 502 can be controlled by an electrode use indication component (e.g., component 320, 421 comprising a timing mechanism as described above) disposed on the electrode patch 500 or in the controller (e.g., controller 120, 420).

Figure 5B:
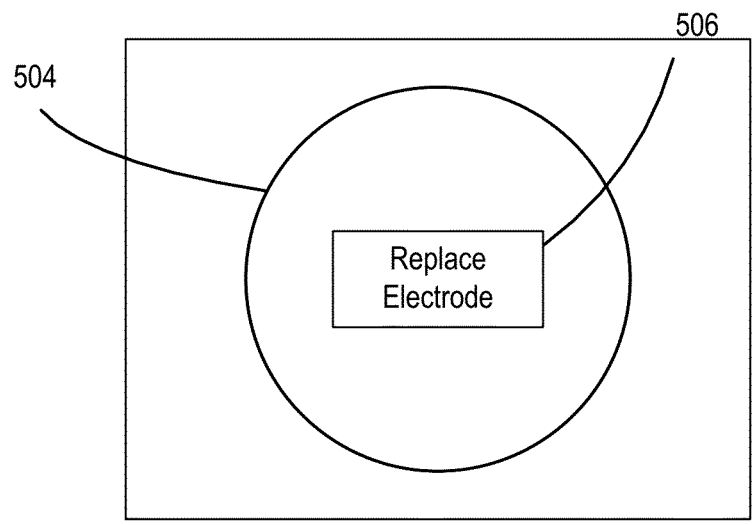

FIG. 5B shows an electrode patch 504 that includes an example electrode patch use indicator. In this example, the electrode use indicator is a display 506 (e.g., an LCD screen) that can present text. For example, the display 506 can provide a message when the predetermined lifespan of the electrode patch has been reached (e.g., "Remove or Replace Electrode"). In some implementations, the display 506 provides a message when the predetermined lifespan of the electrode patch has not yet been reached (e.g., "Electrode OK"). In some implementations, the display 506 may not provide a message when the predetermined lifespan of the electrode patch has not yet been reached but provide a message when the predetermined lifespan of the electrode patch has been reached. In some implementations, the display 506 provides a message when the electrode patch use information indicates that the electrode patch use is within a predefined range of the predetermined lifespan (e.g., 80% of the predetermined lifespan) of the electrode patch (e.g., "Prepare to Remove or Replace Electrode" or "Electrode Use Ending Soon"). In some implementations, the display 506 provides a message when it is unknown whether the predetermined lifespan of the electrode patch has been reached (e.g., "Electrode Status Unknown"). For example, the display 506 can be controlled by an electrode use indication component (e.g., component 320, 421 of FIGS. 3 and 4 comprising a timing mechanism as described above) disposed on the electrode patch 504 or in the controller (e.g., controller 120, 420).

Figure 5D:
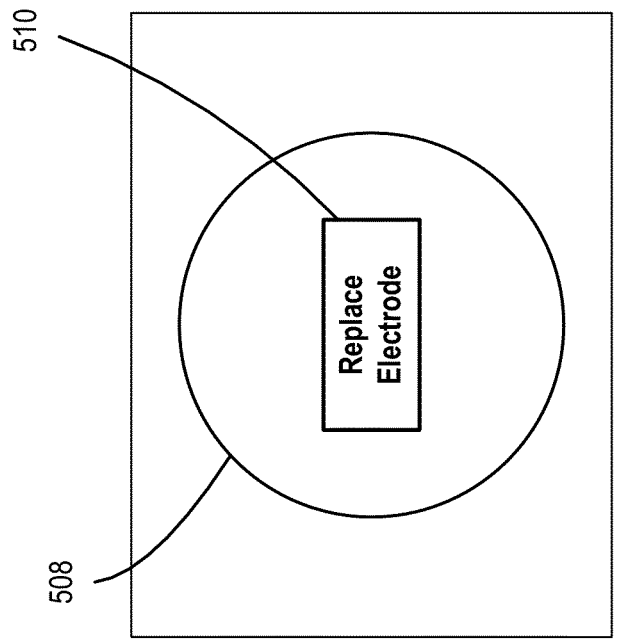
Figure 5C:
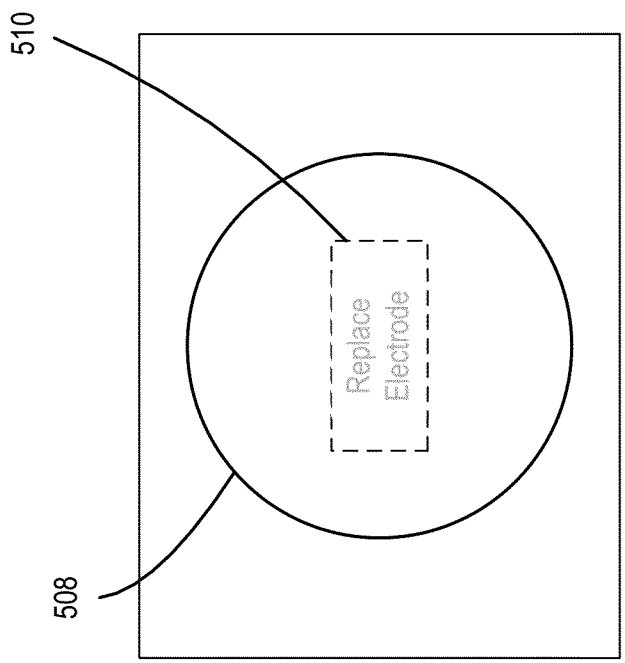

FIGS. 5C-5D shows an electrode patch 508 that includes an example electrode use indicator. In this example, the electrode use indicator is a color-changing material 510. For example, in some implementations, the color-changing material 510 is sensitive to photochemical reactions that occur when the color-changing material 510 is exposed to environmental fluctuations (e.g., exposure to air, exposure to light, etc.). For example, in one implementation, the color changing material 510 comprises at least two portions, e.g., a white vinyl film with a pressure-sensitive adhesive (a front portion) that is placed onto an ink dye-printed backer (a back portion) to cause a timed color change. The self-adhesive vinyl gradually dissolves the ink in the back portion which then slowly migrates into the front portion. After a period of time has elapsed, the white vinyl film changes to a shade of the dye color. In use, a caregiver can apply the front portion to the top of the back portion to initiate the color-changing material 510. When the predetermined lifespan of the electrode patch is reached (e.g., can be configured to be hours, days, or weeks), there is a color change revealing images, messages, or other patterns.

In some implementations, the color-changing material 510 can be applied to the electrode patch 508 in the shape of text (e.g., text reading "Remove or Replace Electrode"). The color-changing material 510 can initially have a color that is the same as the color of the rest of the electrode patch (e.g., white). Thus, the text of the color-changing material 510 may not initially be distinguishable, as indicated by the faded appearance of the color-changing material 510 shown in FIG. 5C. With the passage of time, the text of the color-changing material 510 can change to cause the text to be readable, e.g., as indicated by the black bold text and the solid line representing the color-changing material 510 shown in FIG. 5D. Various chemical and physical techniques known in the art for causing a timed color change in a color-changing material 510 after an initial activation (e.g., exposure to light, oxygen, moisture, and the like) may be employed. In this example, the color-changing material 510 electrode use indicator does not communicate with the electrode use indication component.

In some implementations, a markable surface may be provided, e.g., on the electrode patch, associated cabling and/or wiring, and/or other suitable location associated with the patch, for allowing a person to notate an indication of the predetermined lifespan of the patch. For instance, a label having such a markable surface may be associated with an electrode patch for allowing a caregiver or other person to enter a date and/or time the electrode patch was affixed to the patient, or a date and/or time by which the patch is to be removed or replaced.

Other electrode use indicators can include an audible indication mechanism such as a speaker and associated circuitry. For example, a speaker can be disposed on the controller 120, 420 or the patch for providing the audible alert. For instance, the audible indication of the end of the predetermined lifespan of the patch can be in the form of a periodic or non-periodic voice alert indicating that the patch should be removed or replaced (e.g., a siren or a voice message stating "Remove or Replace Electrode").

Other electrode use indicators can include a vibration or tactile indication mechanism such as a vibration device and associated circuitry. For example, the vibration device can be disposed on the controller 120, 420 or the patch for providing the vibration alert to the patient or other user. For instance, the vibration indication can be in the form of a periodic or non-periodic vibration alarm indicating that the patch should be removed or replaced.

Example Electrode Patch—Electrode Use Indication Component Included in Patch

In some implementations, the electrode use indication component can be located somewhere other than in the medical device controller 120, 420. For example, at least some of the circuitry that makes up the electrode use indication component can be included in one or more of the electrode patches. FIG. 6 shows an example of an electrode patch 600 that includes an electrode use indication component 602. The electrode use indication component 602 can be configured to operate in a manner substantially similar to that of the other electrode use indication components described herein (e.g., electrode use indication component 320, 421 as shown in FIGS. 3 and 4). In some examples, the electrode use indication component 602 that is included in the electrode patch can include a battery power source for powering the circuitry of the electrode use indication component 602 independent of any other power source. In this way, the component need not rely on power from the battery in the medical device controller 120, 420.

Electrode Use Indication Component—Integrity of the Patch

While the electrode use indication component has thus far been largely described as being configured to determine information related to a lifespan of one or more electrode patches, in some implementations, the electrode use indication component can be configured to determine information related to an integrity of the electrode patch. As noted above, for example, the integrity of the electrode patch may be monitored in the form of an integrity measure. As such, the integrity measure can be indicated (visually or otherwise) through the indicating mechanism. For example, the indicating mechanism based on an integrity measure of the electrode patch operates in a similar manner as described above (see, e.g., electrode use indicators of FIGS. 5A-D and 6). The electrode use indication component can cause an indicating mechanism to indicate that an electrode should be removed or replaced when the integrity measure transgresses a threshold value. In this manner, information related to the integrity of the electrode patch can be used to determine whether and/or when the electrode patch should be removed or replaced. As such, the electrode use indication component can determine that the electrode patch should be removed or replaced based on an underlying condition of the electrode patch rather than an end of a predetermined lifespan of the electrode.

For example, in various implementations, an integrity of the electrode patch can be a signal integrity or a physical integrity.

Signal Integrity

For example, the integrity measure may reflect a signal integrity of the electrode patch. Such signal integrity can be associated with an impedance measurement that is experienced by one or more electrodes of the electrode patch. An underlying condition of the electrode patch-skin interface can therefore be indicated through the use of signal integrity measurements. For instance, as discussed above, it may be desirable to minimize the amount of impedance between the one or more electrodes of the electrode patch and the patient's skin seen by a monitor. If an electrode patch is experiencing an impedance that is unacceptable (e.g., outside of a predefined range or in excess of a predetermined threshold as described below), the electrode use indication component may determine that the electrode patch should be removed or replaced, and such a determination can be said to have been made based on a signal integrity of the electrode patch. For example, this determination can be made irrespective of the underlying cause of the unacceptable impedance.

Figure 7:
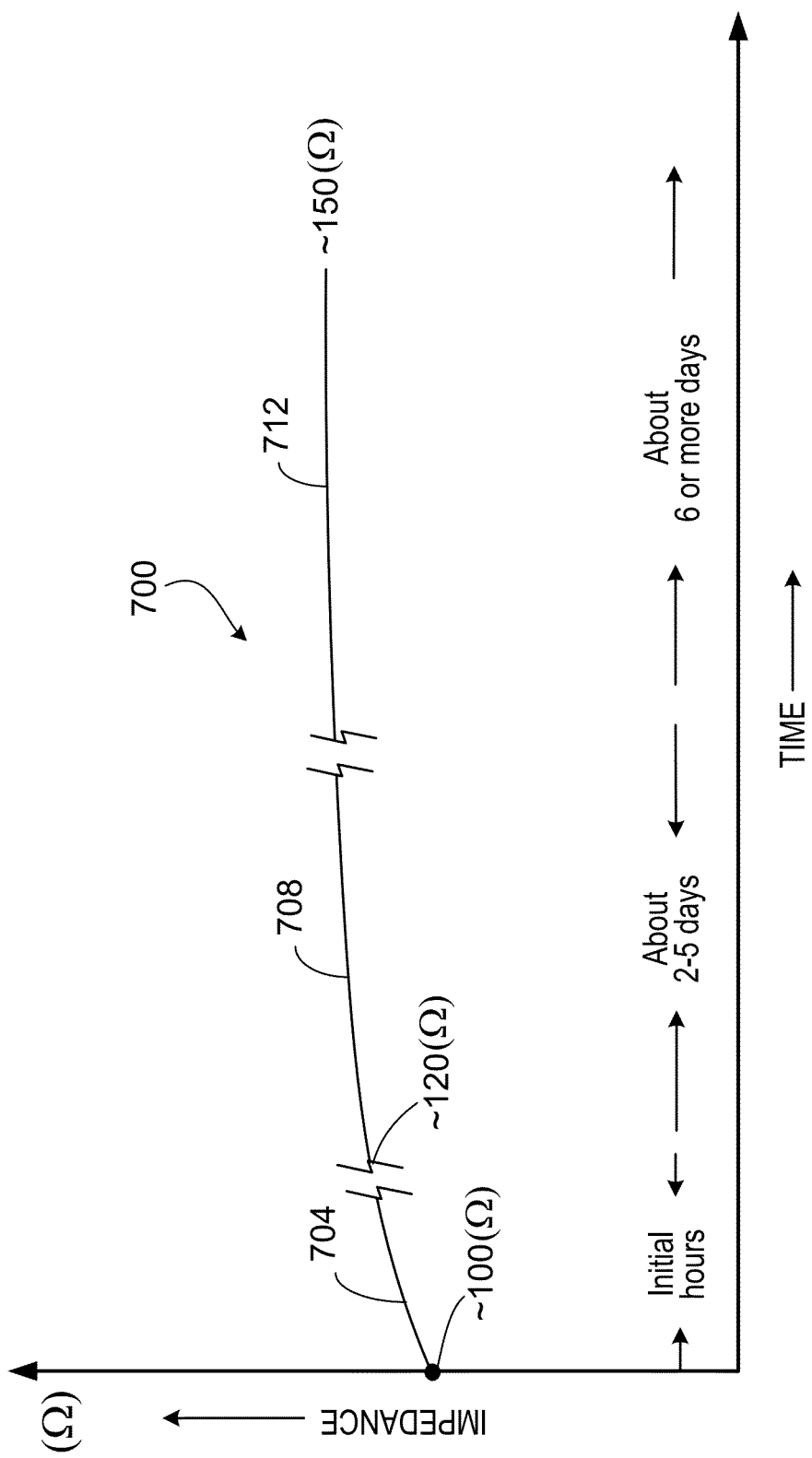
FIG. 7 shows a graph illustrating measured impedance as a function of time.

FIG. 7 shows an example graph 700 illustrating a plurality of ranges of impedance values over a period of time for a hypothetical patient using conductive gel based electrode patches that are configured for long term use (e.g., up to a week or more of use). For instance, such a long term electrode patch can be configured to be continuously or substantially continuously worn by a patient for an extended period of time. One example of such an electrode patch is described in the '096 patent publication.

The graph 700 illustrates typical ranges of expected impedance values for a patient over the period of electrode patch use based on experimental data from test groups of patients. For example, two sensing electrodes in the electrode patch can completes a circuit that includes the medical device controller 120, 420 and the patient. The portion of the circuit that includes the patient's body causes the electrodes to sense an impedance known as the patient's transthoracic impedance. For conductive gel based electrode patches, typical acceptable patient impedance values can be in a range of 20-140 Ohms. Beyond this range, signals from sensing electrodes may be deemed unreliable. For therapy electrodes, the higher impedance values can result in insufficient energy being delivered to the patient.

The graph 700 includes a first portion 704, a second portion 708, and a third portion 712. The first portion 704 of the graph 700 shows initial changes in impedance values within a few hours of affixing the electrode patch on the patient (e.g., from about 100 Ohms to about 120 Ohms). As shown in the second portion 708 of the graph 700, over the next few days (e.g., 2-5 days), the impedance value creeps upwards at a slower rate than during the first portion 704 (e.g., from about 120 Ohms to about 130 Ohms). Finally, towards an end of a typical electrode patch use period (third portion 712), the impedance value is shown to have crept up to unacceptable levels (e.g., 140-150 Ohms or more). For the example long term electrode patch described above, a predetermined lifespan of the patch can be selected to be 7 days. Accordingly, in some implementations, regardless of the underlying impedance values, after a period of use when the predetermined lifespan is reached, the electrode use indicator can indicate that the electrode patch should be removed or replaced as discussed above.

An integrity measure of the electrode patch can be in the form of monitoring the impedance experienced by one or more electrodes of the patch. Accordingly, in some implementations, alternatively or in addition to a predetermined lifespan of the patch, the electrode use indicator may indicate that the electrode patch should be removed or replaced when the electrode use indication component (e.g., electrode use indication component 320, 421) determines that an impedance value of one or more electrodes of the patch is outside a predefined range of impedance values (e.g., 50-150 Ohms) or has transgressed a predetermined threshold, e.g., 150 Ohms. In some implementations, the electrode use indication component 320, 421 may be configured such that at least two electrodes of a patch experience impedance outside the predetermined range before the electrode use indicator indicates that the patch should be removed or replaced.

The electrode patch may experience the increased impedance for a number of reasons. For example, the electrode patch's hydrogel may have begun to dry up. When the electrodes make contact with the patient, an amount of impedance of the electrical path between the electrode patch and the patient is initially experienced. Over time, this impedance value gradually increases until the impedance value is such that the electrode patch should be removed or replaced.

In various examples, a change in the integrity measure, e.g., an increase in impedance value above a threshold value, may be temporary. Depending on the situation, it may be desirable to indicate whether the patch can continue to be used or if it should be removed or replaced. For example, in an implementation, if the electrode patch has briefly fallen off or otherwise become unattached from the patient's skin and is returned to the patient's skin, it may be desirable that the patch be permanently removed or replaced with a new patch. In such a situation, the electrode use indicator can be configured to indicate that the electrode patch should be removed or replaced. For instance, if the indicator is a light source (e.g., which lights up to indicate that the patch should be removed or replaced as described above), such indicator may continue to remain lit up to indicate that the patch should be removed or replaced on detecting that the patch has fallen or otherwise become unattached from the patient's skin.

In some implementations, it may be desirable to cause the electrode use indication component to indicate that patch use may continue despite an increase in impedance over the threshold value. For example, the impedance experienced by one or more electrodes of a patch may temporarily increase, transgressing the threshold value for a period of time, even as the electrode patch remains firmly on the patient's skin. It may be desirable to set a range where if the integrity measure, e.g., the impedance in this case, temporarily transgresses the threshold value, electrode patch use may continue. In an implementation, to accommodate such temporary transgressions, an acceptable range of the impedance values may be temporarily raised by a permissible amount. For example, it may be tolerable to allow the impedance to exceed the threshold value by, e.g., about 10% of the threshold value, for a predetermined period of time, e.g., one hour. In such cases, the electrode use indicator can be configured to stop indicating that the patch should be removed or replaced when the impedance returns to the normal range, e.g., an LED indicator that had lit up to indicate that the electrode patch should be removed or replaced can be turned off to indicate that the patch can continue to be used. Alternatively, the LED indicator may not light up until the predetermined period of time (one hour in the example above) has elapsed.

Physical Integrity

A physical integrity of the patch can be associated with the physical geometry and/or the structural nature of the electrode patch. If an electrode patch or one or more electrodes of the patch is structurally compromised (e.g., the electrode patch is warped, peeling off the patient, etc.), the electrode use indication component may determine that the electrode patch should be removed or replaced. In some implementations, the electrode use indication component determines an integrity measure for the patch based on information relating to the physical integrity of the electrode patch. As noted above, such information can also include impedance measurements associated with one or more electrodes of the electrode patch as discussed above.

The electrode use indication component can analyze impedance measurements to determine that a portion of the electrode patch is not in good contact with the patient's skin. For example, briefly referring back to FIG. 7, electrode patches with good physical integrities (e.g., substantially flat electrode patches that are sufficiently affixed to the patient's skin) may experience an impedance as shown in the graph 700 with respect to each electrode on the patch. Over time, some or all of the electrodes on the patch may develop poor physical integrities (e.g., become warped or become loose such that the electrodes are not sufficiently affixed to the patient's skin). In such situations, impedance values associated with one or more of the electrodes of the patch begin to approach the threshold value.

In certain implementations, it may be desirable to track the impedance values corresponding to each electrode in a multi-electrode patch. For instance, it may be desirable to remove or replace an electrode patch when any electrode of a patch experiences an impedance above the threshold value. In other cases, it may be desirable to have a phased response to the electrode use indication. For instance, if only one electrode is experiencing high impedance, it may be that the electrode only needs to be appropriately adjusted rather than removing or replacing the entire patch. As such, there may be a plurality of electrode use indicators on a patch, each corresponding to a plurality of electrodes on the multi-electrode patch. In an implementation, there may be two or more light sources (e.g., LED indicators) each corresponding to a different electrode in the patch. When one of the plurality of electrodes is experiencing a high impedance condition (e.g., impedance above the threshold value) the corresponding light source can be caused to light up and remain lit until the issue can be resolved.

In some implementations, a conductive adhesive gel layer or the adhesive layer that facilitates the electrical connection between the electrode patch and the patient may deteriorate and/or lose its binding strength over time. For example, the binding strength of the adhesive gel or the adhesive material can diminish due to the patient sweating while wearing the electrode patch, exposure of the electrode patch to the air, exposure of the electrode patch to a high humidity environment, exposure of the electrode patch to moisture in an amount beyond a predetermined threshold, and/or the electrode patch being removed and reapplied, among other reasons. The diminished binding strength may cause the connection between the electrode patch and the patient to be weaker than it was when the electrode patch was initially affixed to the patient, thereby resulting in the electrode patch experiencing increased impedance. In this way, the electrode patch may experience increased impedance as it becomes dirty (e.g., from dirt, dust, hair, moisture, skin cells, etc.).

Example Electrode Patch

Figure 8B:
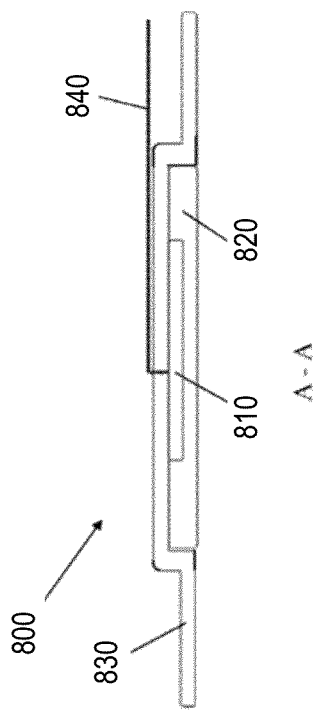
FIGS. 8A-8B show an example of an electrode patch that can be used with the medical devices described herein.
Figure 8A:
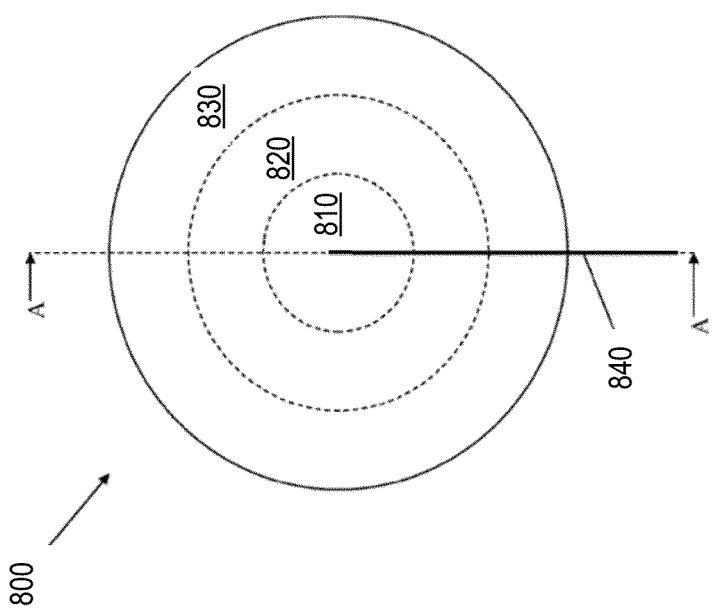

In some implementations, the electrode patches includes both a conductive gel layer and a conductive adhesive layer, which are separate layers. FIGS. 8A and 8B show respective plan and cross-sectional views of an example of an electrode patch that can be used with the medical devices described herein. The electrode 800 includes a conductive element 810 (e.g., a metal film), a conductive gel layer 820 (e.g., a hydrogel layer) that substantially surrounds the conductive element 810, an adhesive film layer 830 that substantially surrounds the conductive gel layer 820, and an electrical conductor 840 (e.g., a metal wire) that electrically connects the conductive element 810 to the medical device. The adhesive film layer 830 can include an adhesive on at least a portion of a surface thereof and may be used to adhere the electrode 800 to the skin of the patient and to maintain the conductive gel layer 820 in electrical contact with the skin of the patient.

Figure 9:
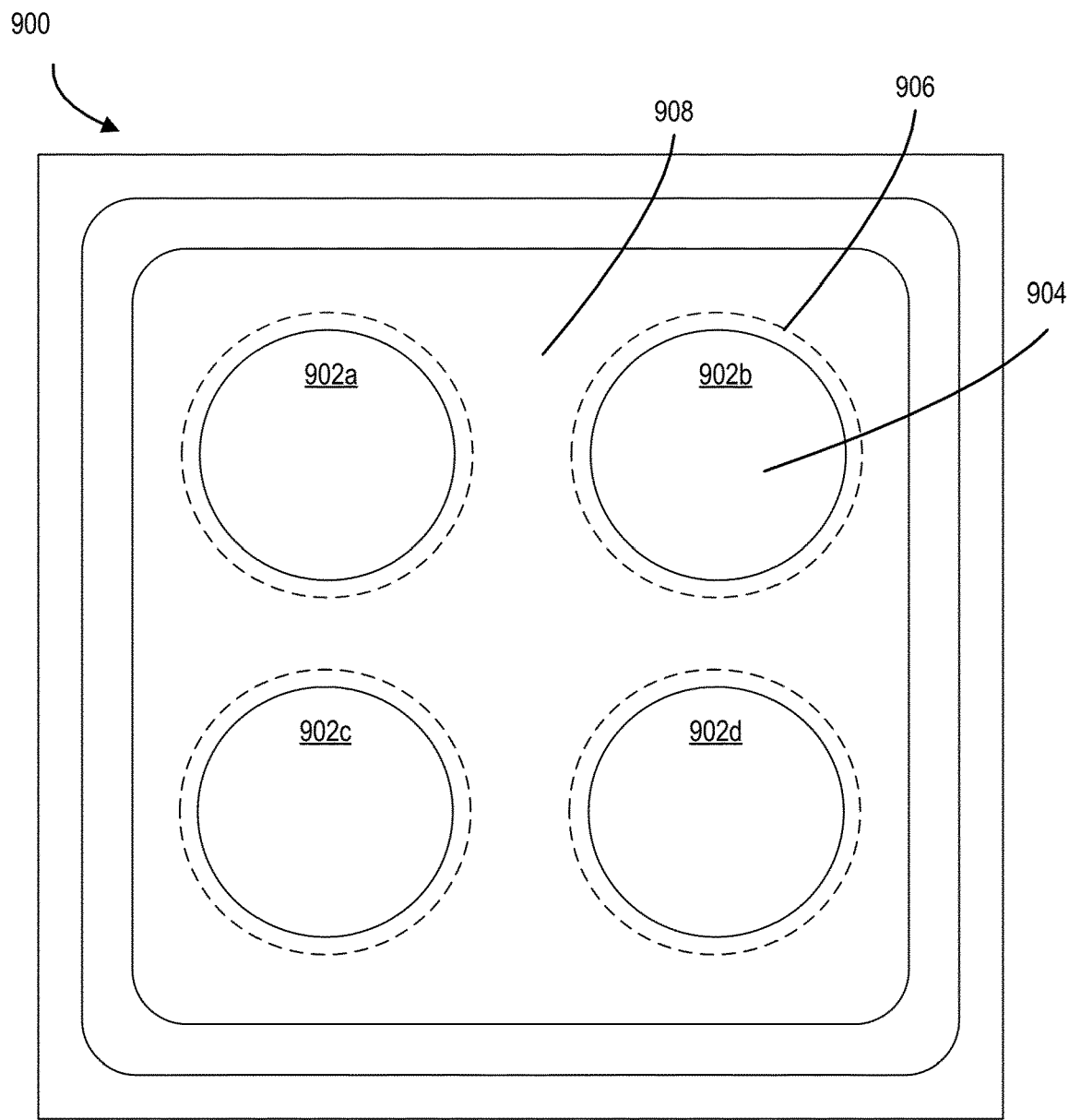
FIG. 9 shows an example of an electrode patch that can be used with the medical devices described herein.

In some implementations, multiple electrodes can be included on a single electrode patch as noted above. FIG. 9 shows an example of an electrode patch 900 that can be used with the medical devices described herein. The electrode patch 900 includes multiple electrodes 902a-d. The multiple electrodes 902a-d of the electrode patch 900 are sometimes generally referred to as multiple segments. Each of the electrodes 902a-d can include a conductive element 904 and a conductive gel layer 906. The electrodes 902a-d may share a common adhesive film layer 908. In some implementations, the conductive gel layer 906 and the adhesive film layer 908 are together configured to operate in a fashion similar to the conductive adhesive layer described above.

When the physical integrity of the electrode patch 900 becomes compromised (e.g., a void forms between the electrode patch 900 and the skin of the patient, or the electrode patch 900 beings to peel off of the patient), the impedance that is seen by the electrodes 902a-d may be affected. For example, when a void exists between the electrodes 902a-d and the patient's skin, a transverse electrical current may flow a greater distance across the conductive gel layer 906 of the electrode patch 900, thereby causing the electrodes 902a-d to experience higher impedance values. Further, the presence of the void presents a portion of air into the electrical path and can cause the electrodes 902a-d to experience higher impedance values.

In some implementations, each of the electrodes 902a-d is part of its own electrical path that includes the electrode, a portion of the patient's body, and a reference point (e.g., another electrode). For example, four separate impedances of four separate electrical paths are measured—one for the first electrode 902a and the reference point; one for the second electrode 902b and the reference point; one for the third electrode 902c and the reference point; and one for the fourth electrode 902d and the reference point. Each of these impedance values may be represented in a graph in a similar manner as described above with respect to FIG. 7. In some implementations, if one of the electrodes is not in contact with the patient's skin (e.g., due to the electrode patch being peeled off), the impedance related to that electrode represents a substantially open circuit condition. In some implementations, if one of the electrodes is not in intimate contact with the patient's skin (e.g., due to the formation of a void between the electrode and the skin or due to warping of the electrode patch), the impedance related to that electrode patch may have a value that is outside of a satisfactory range (e.g., greater than 200 ohms). Based on the measured impedances, the electrode use indication component can determine that the electrode patch 900 has unsuitable physical integrity, and consequently determine that the electrode patch 900 should be removed or replaced.

In some implementations, if the electrode patch 900 has an acceptable physical integrity, the impedance measurements associated with each of the electrodes 902*a-d* may have values that are substantially similar (e.g., within 1-5 Ohms of each other). Substantially similar impedance measurements may indicate that each of the electrodes 902*a-d* are intimately in contact with the patient's skin. In contrast, if the electrode patch 900 has an unacceptable physical integrity, the impedance measurements associated with each of the electrodes 902*a-d* may have values that differ by an amount beyond a threshold (e.g., 50 Ohms). Such a difference in the impedance measurements may indicate that one or more of the electrodes 902*a-d* do not make sufficient contact with the patient's skin. The insufficient contact with the patient's skin may be due to the electrode peeling, the electrode's adhesive deteriorating, a void forming between the electrode and the patient's skin, and/or the electrode patch being warped, each of which may prevent the electrode patch from making flush contact with the patient's skin. For example, if the impedance related to the first electrode 902*a* is 120 Ohms and the impedance related to the second electrode 902*b* is 175 Ohms, one of the electrodes (e.g., the electrode associated with the higher impedance value) may be physically compromised. Thus, the electrode use indication component may indicate that the electrode patch 900 should be removed or replaced.

Further non-limiting details of electrodes and multi-electrode patches that can be used along with the systems and techniques described herein can be found in '096 patent publication.

Figure 10:
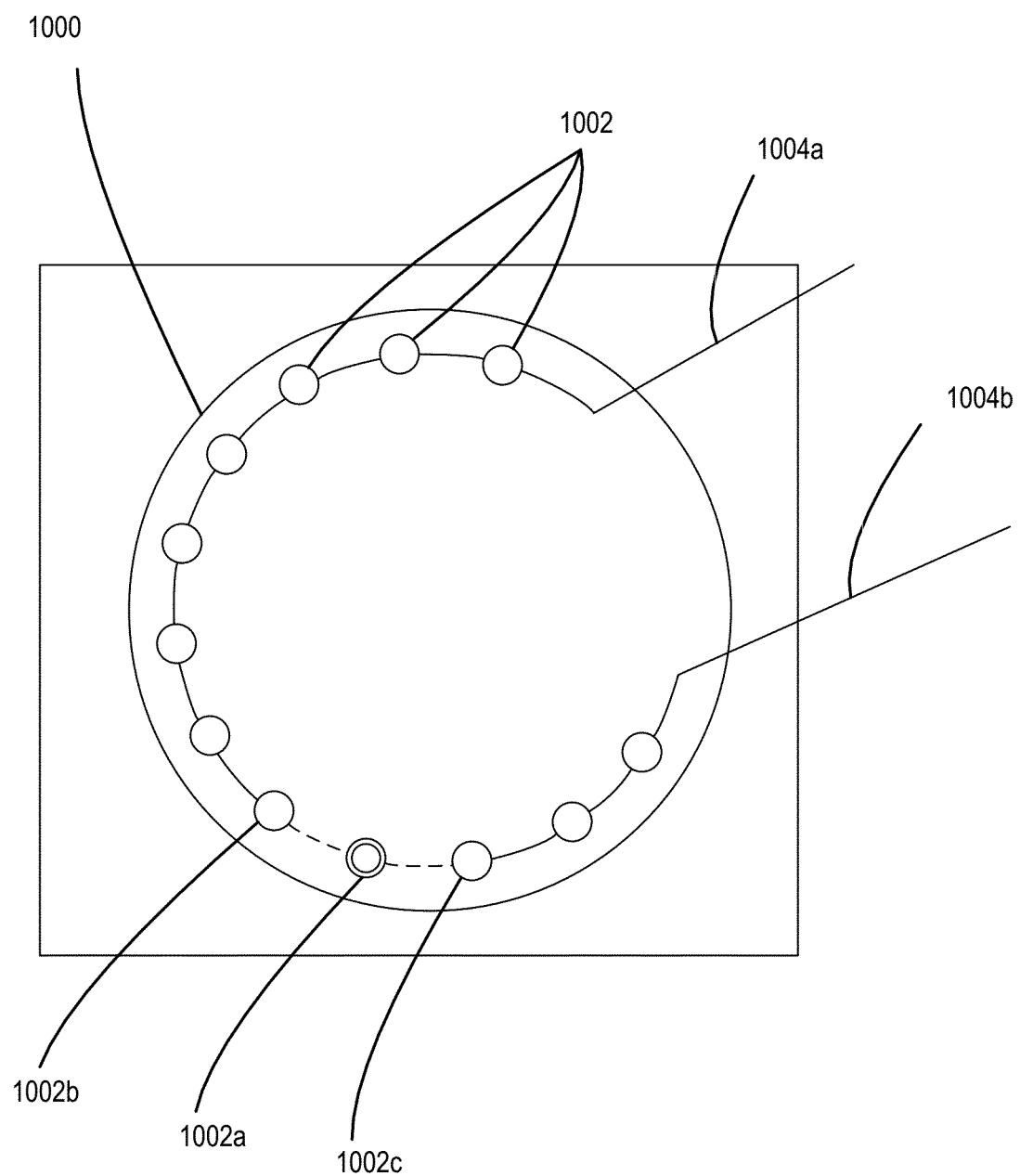
FIG. 10 shows an example of an electrode patch that includes a plurality of buttons.

In some implementations, a physical integrity of an electrode patch can be monitored based a ring circuit disposed in the patch. FIG. 10 shows an example of an electrode patch 1000 that includes a plurality of conductive buttons 1002 around the peripheral edge of the electrode 1000 arranged in the form of a ring. The buttons may be arranged in any manner to achieve similar results as described herein. When the buttons 1002 are engaged (establishing that the corresponding portion of the patch is in contact with the patient's skin), the buttons 1002 are electrically connected to each other forming a conductive ring around the peripheral edge of the electrode 1000. In some implementations, the buttons 1002 comprise a metallic conductive material that when engaged (e.g., pressed) establishes electrical connectivity with other buttons 1002 and the rest of the conductive ring.

A first end of the ring terminates in a first lead 1004*a*, and a second end of the ring terminates in a second lead 1004*b*. The status of the ring circuit between the first 1004*a* and second 1004*b* leads can be monitored. For example, when all of the buttons 1002 are engaged (e.g., all of the buttons 1002 are electrically connected to each other) the ring circuit is closed. As the physical integrity of the electrode 1000 diminishes (e.g., due to curling or warping), some portions of the electrode 1000 may no longer be in intimate contact with the patient's skin. Consequently, buttons 1002 that are positioned near such portions of the electrode 1000 are disengaged.

When the non-engaged button 1002*a* is not engaged, the ring circuit between the first lead 1004*a* and the second lead 1004*b* is broken. When the open circuit condition is detected, the electrode use indication component can determine that the physical integrity of the electrode patch is no longer acceptable and should be removed or replaced.

Example Electrode Use Indicators—Remaining Lifespan

While the electrode use indicator has been described as being configured to indicate an end of a predetermined lifespan of the electrode, in some implementations, the electrode use indicator can be configured to indicate a lapsed and/or remaining lifespan of the electrode.

In some implementations, the elapsed and/or remaining lifespan is based on the predetermined lifespan of the electrode patch. For example, if the predetermined lifespan of the electrode patch is 48 hours, and the electrode use indication component determines that 12 hours of the predetermined lifespan of the electrode patch is remaining, the electrode use indicator indicates that 75% of the electrode patch's lifespan remains. For example, if the predetermined lifespan of the electrode patch is 48 hours, and the electrode use indication component determines that 12 hours of the predetermined lifespan of the electrode patch has elapsed, the electrode use indicator indicates that 25% of the electrode patch's lifespan has elapsed. In some examples, the electrode use indicator can be based on a running counter indicating an elapsed duration of use of the patch (e.g., 12 hours of use has elapsed). In some examples, the electrode use indicator can be based on a running counter indicating a remaining duration of use of the patch (e.g., 36 hours of use remains). In some cases, more than one mode of indication may be employed. For instance, the electrode use indicator can indicate both that a predetermined percentage of patch lifespan remains or has elapsed and also indicates an amount of elapsed or remaining duration of use of the patch. Further, while the examples described herein are given in terms of duration and/or time, other types of metrics and/or quantities can be used to indicate the remaining or elapsed lifespan. For instance, an elapsed or remaining amount of cumulative current passed by one or more electrodes of the patch can be used to indicate the elapsed and/or remaining lifespan of the patch.

In some implementations, the remaining lifespan is based on the integrity measure of the electrode patch. For example, the remaining lifespan can be based on the signal integrity of the electrode patch. In some implementations, for example, an impedance of 120 Ohms experienced by the electrode may represent that the electrode patch has all of its lifespan remaining, and an impedance of 150 Ohms experienced by the electrode patch may represent that the electrode patch has none of its lifespan remaining. If the electrode use indication component determines that the electrode patch is experiencing an impedance of 130 Ohms, the electrode use indicator may indicate that about 67% of the electrode's lifespan remains.

Figure 11A:
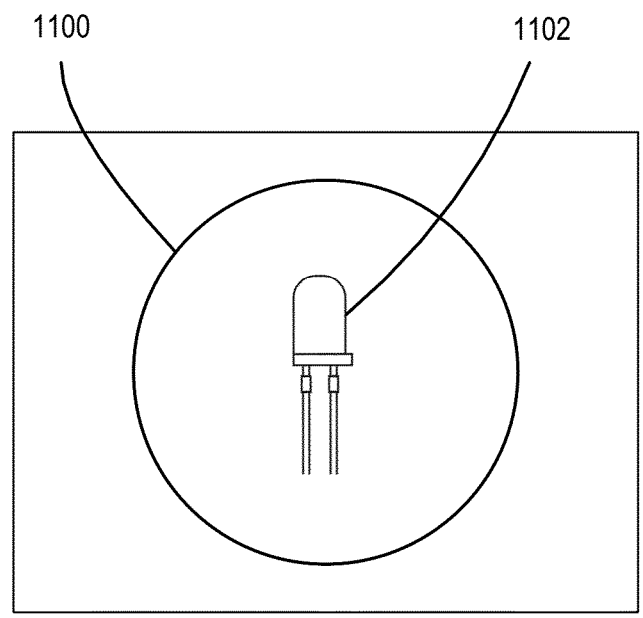
FIGS. 11A-11C show electrodes with example electrode use indicators.

FIG. 11A shows an electrode patch 1100 that includes an example electrode use indicator. In this example, the electrode use indicator is a light source 1102 (e.g., an LED) that can emit light in various colors and/or in various brightnesses. For example, the light source 1104 can emit a green light when the remaining lifespan of the electrode 1100 is relatively high (e.g., 80% or more of the lifespan remaining), emit a yellow light when the remaining lifespan of the electrode 1100 is moderate (e.g., 40-80%), emit an orange light when the remaining lifespan of the electrode 1100 is relatively low (e.g., 5-40%), and emit a red light when the remaining lifespan of the electrode 1100 is depleted or almost depleted (e.g., 0-5%). In some implementations, the brightness of the light source 1102 can indicate the remaining lifespan of the electrode 1100. For example, the light source 1102 can emit no light when the remaining lifespan of the electrode 1100 is relatively high, emit a bright light when the remaining lifespan of the electrode 1100 is depleted or almost depleted, and emit lights of various brightnesses to indicate that the remaining lifespan of the electrode 1100 is somewhere in between.

Figure 11B:
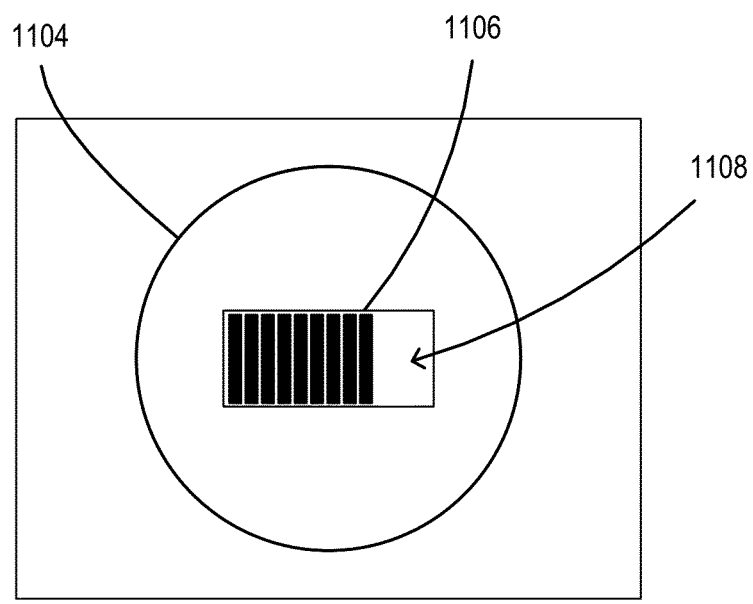

FIG. 11B shows an electrode patch 1104 that includes an example electrode use indicator. In this example, the electrode use indicator is a display 1106 (e.g., an LCD screen) that can present pictures, symbols, animation, and/or text. For example, the display 1106 can provide a gauge 1108 that represents the remaining lifespan of the electrode patch 1104. In the example shown in FIG. 11B, the electrode patch 1104 has about 75% of its lifespan remaining. In some implementations, the display 1106 can present text that indicates the remaining lifespan of the electrode 1104 as a percentage.

Figure 11C:
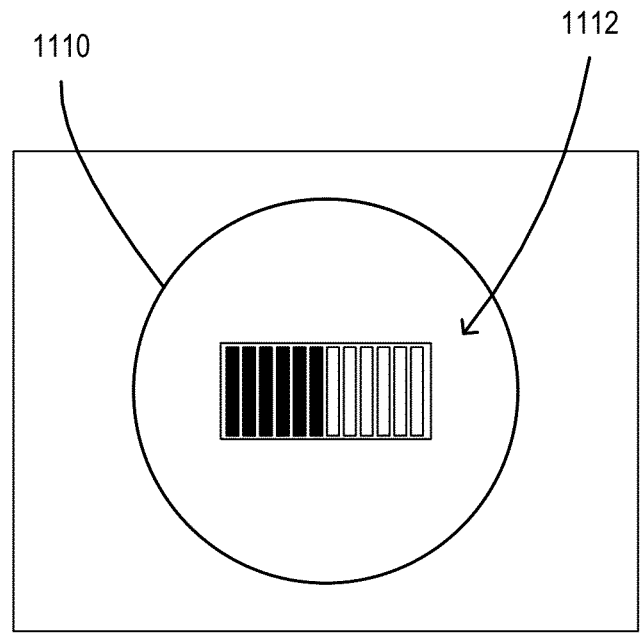

FIG. 11C shows an electrode patch 1110 that includes an example electrode use indicator. In this example, the electrode use indicator is a color-changing material 1112. For example, the color-changing material 1112 may be sensitive to photochemical reactions that occur when the color-changing material 1112 is exposed to environmental fluctuations (e.g., exposure to air, exposure to light, etc.). The color-changing material 1112 can initially have a color that is different than the color of the rest of the electrode patch 1110. Thus, the color-changing material 1112 may initially be visible to an observer. In this example, the color-changing material 1112 is initially black. When an environmental fluctuation occurs (e.g., exposure to oxygen or light for a particular amount of time), a photochemical reaction can cause the color-changing material 1112 to turn a different color, such as the color of the rest of the electrode (e.g., white), thus causing the color-changing material 1112 to be indistinguishable. In other implementations, the color changing scheme described above may be reversed, e.g., initially the color-changing material 1112 may initially be indistinguishable from the rest of the electrode patch (e.g., white) and then change to a color that is different from the color of the electrode patch (e.g., red or black) when the patch is to be removed or replaced.

The color-changing material 1112 can be applied to the electrode patch in the shape of a gauge. The color-changing material 1112 can have multiple portions (e.g., segments of the gauge) that can each have a different degree of sensitivity to photochemical reactions. For example, the leftmost segment of the gauge may have the lowest sensitivity, the rightmost segment may have the highest sensitivity, and the segments in between may have sensitivities proportional to their relative positions. Because each segment of the gauge has a different sensitivity, the amount of time required for each segment to change from black to white is different. Initially, every segment is black. As the more-sensitive segments (e.g., the segments on the right of the gauge) are exposed to environmental fluctuations, they begin to change from black to white. Starting with the rightmost segment and ending with the leftmost segment, the segments sequentially change from black to white. The number of remaining black segments represents the remaining lifespan of the electrode 1110. In this example, the electrode use indicator indicates that about 50% of the lifespan of the electrode 1110 remains.

While certain implementations have been described, other implementations are possible.

While the electrode use indicator has been described as being positioned on one or more of the electrodes, in some implementations, the electrode use indicator could be positioned elsewhere. For example, the electrode use indicator may be positioned on the medical device controller.

In some implementations, the components described with reference to FIGS. 3 and 4 (e.g., the cardiac event detector and/or the electrode use indication component) can be implemented using hardware or a combination of hardware and software. For example, in some implementations, the cardiac event detector and/or the electrode use indication component is implemented as a software component that is stored within the data storage and executed by the processor.

In some implementations, the medical devices described herein can include one or more additional sensors and corresponding sensor interface components. Examples of additional sensors can include a body temperature sensor, a respiration sensor, an environmental sensor (e.g., an atmospheric thermometer, an airflow sensor, a video sensor, an audio sensor, a locational sensor, a hygrometer, etc.), or a motion sensors (e.g., an accelerometer, a gyroscope, etc.). In some implementations, the additional sensors are wirelessly coupled to the medical device controller 120, 420.

In some implementations, the electrode patch includes a salinity sensor that is configured to sense perspiration. The electrode use indication component can interact with the salinity sensor to determine when and/or how much the patient is sweating. Based on the measured sweat, the electrode use indication component can determine whether the electrode patch may be in condition for removal or replacement. For example, the salinity sensor may collect and measure sweat content using paper microfluidics. For instance, a paper material can wick sweat and pass it through the salinity sensor to detect, e.g., a concentration of sodium and/or chloride ions, before passing the sweat to a fluid-absorbing hydrogel. In some examples, a quantity of the fluid can be used to determine how much the patient is sweating and to set a threshold quantity at which the electrode patch should be removed or replaced. For example, an expansion in the size of the hydrogel material can correlate to the amount of sweat absorbed. For example, the salinity sensor can include a lead coated with an ion-selective membrane and a reference material (e.g., silver chloride). The coating for the ion-selective membrane can be a polymer (e.g., cross-linked polyethylene) through which ions would not be able to easily penetrate, along with an ionophore molecule that allows passage of only one type of ion. For example, the ionophore can allow sodium to easily penetrate into the polymer material. Because sodium is positively charged, a voltage begins to build up over time based on the accumulated sodium ions. A voltage buildup between the polymer material and the reference material can include an amount of sodium and therefore sweat.

In some implementations, the medical devices can include one or more additional therapy delivery components (e.g., in addition to therapy electrodes) and corresponding therapy delivery interface components. Examples of additional therapy delivery components can include a capacitor, a pacing electrode, and/or a mechanical chest compression device. In some implementations, the additional therapy delivery components are wirelessly coupled to the medical device controller.

While the medical devices described herein have been described as including a variety of components, in some implementations, the functionality of one or more of the components may be incorporated into one or more other components. For example, in some implementations, the functionality of the electrode use indication component and/or the cardiac event detector may be incorporated into the processor. In some implementations, the electrode use indication component and/or the cardiac event detector may themselves be processors. In some implementations, the electrode use indication component and/or the cardiac event detector may be independently functional (e.g., without receiving instructions from the processor).

While the medical device controller 120, 420 has been described as including a processor, in some implementations, the processor is included in another portion of the medical device (e.g., outside of the medical device controller 120, 420). In some implementations, the medical device includes multiple processors, any of which may be located inside or outside of the medical device controller. In some implementations, a processor is included in an external pod (e.g., the connection pod 130 of FIG. 1.)

While the medical devices described herein (e.g., the wearable medical device 100 of FIG. 1 and the cardiac monitor 400 of FIG. 4) have been described and shown as including a particular number of electrodes positioned at particular locations on the patient, the number and/or positions of the electrodes can vary to best suit the particular application.

In some implementations, the medical devices described herein are configured to communicate with another device (e.g., a smartphone, a personal digital assistant, a tablet, etc.) over a network. The communication network may be wired or wireless.

While the determination of whether an electrode patch should be removed or replaced has been described as being based on whether the experienced impedance is beyond a threshold (e.g., 150 Ohms), in some implementations, the determination could be based on whether the experienced impedance transcends a baseline or threshold impedance by a particular amount. The impedance of the body can vary from patient to patient (and, e.g., from electrode to electrode). Thus, the impedance experienced by one or more electrodes of a patch can depend on the physiology of the particular patient. Other factors can also affect the impedance experienced by the electrode patches, such as the precise placement of the patches. Accordingly, in some implementations, a determination of when the patch should be removed or replaced can be based on how much the impedance experienced by the one or more electrodes of the patch has changed over time. For example, after two patches are applied to a patient, the experienced impedance as seen by the patches may level off at 155 Ohms. While it is possible that such an impedance indicates poor signal integrity, it is also possible that the particular patient happens to have an atypically high bodily impedance. If the patient has an atypically high bodily impedance, it would not be proper to replace the electrodes with new electrodes because the new electrodes would encounter the same a typically high bodily impedance. Rather, the value at which the impedance leveled off (e.g., 155 Ohms) can be used as a baseline or threshold, and the electrode use indication component can be configured to determine that one or both of the patches should be removed or replaced if the experienced impedance increases by a particular amount beyond the baseline. In some implementations, the particular amount can be a fixed value (e.g., 10 Ohms) or a percentage of the baseline impedance (e.g., 10% of the baseline impedance, or 15.5 Ohms in excess of the baseline impedance).

In some implementations, the impedance experienced by the electrodes undergoes signal processing before it is made available to the electrode use indication component. For example, the experienced impedance may be averaged or may be represented as a quadratic mean. In some implementations, the impedance is determined based on a moving average or a root mean square of impedance measurements. In this way, inaccurate impedance values can be filtered out so that the electrode use indication component does not determine that the electrodes should be removed or replaced based on an outlier impedance value.

In some implementations, the electrode patch includes a consumable circuit component. When the electrode patch is in use (e.g., when electrical current is running through the electrode), the consumable circuit component is electrochemically consumed (e.g., through oxidation and/or reduction) until it is depleted. The electrode use indication component can be configured to determine the amount in which the component has been consumed and use this information to infer a condition of the electrode. For example, the electrode use indication component can provide an indication to the electrode use indicator that the electrode patch should be removed or replaced when the consumable circuit component has been consumed. In some implementations, the consumable circuit component is consumed while the electrode patch is attached to the patient (e.g., even if there is little or no electrical current running through the electrode).

In some implementations, the electrode use indication component can be configured to interact with a strain sensor to determine the physical integrity of the electrode. For example, in some implementations, the electrode patch can include a strain gauge that includes a strain sensitive metal foil pattern. When the electrode patch is deformed (e.g., warped, peeling, curling, etc.), the metal foil also deforms, and the deformation causes the overall length of the metal foil pattern to change. The physical change in the metal foil pattern causes the end-to-end resistance of the pattern to change. An output voltage across terminals of the metal foil pattern corresponds to the change of resistance, and therefore is indicative of an amount of strain measured by the strain gauge. When the amount of strain exceeds a predetermined threshold, the electrode use indication component can determine that the physical integrity of the electrode patch is unsuitable, and thus provide an indication to the electrode use indicator that the electrode patch should be removed or replaced.

In some implementations, the electrode use indicator can be located at a location remote from the medical device. For example, the electrode use indicator may be located at a remote medical facility, such as a nurse's station, where the nurse can be informed that an electrode patch needs to be removed or replaced. In some implementations, the electrode use indicator is positioned at a location that is convenient to or frequented by the patient or the patient's caregiver, such as in the patient's room, on a television, on a refrigerator, etc. In some implementations, the electrode use indicator is removable (e.g., removable from the monitor, removable from the electrode, etc.). For example, the electrode use indicator may initially be affixed to the electrode. The patient may remove the electrode use indicator from the electrode patch and affix it to a status board (e.g., on a wall, on a calendar, on a chart, on a refrigerator, etc.). The status board may include electrode use indicators for multiple electrodes. The status board may be at locations that are convenient to or frequented by the patient and/or the caregiver. The patient or the caregiver can look at the status board to determine if/when various electrodes should be removed or replaced. Similarly, a medical facility can maintain a status board that includes multiple electrode use indicators for various patients. The status board can be positioned at a central location. For example, a caregiver may have his or her own status board that includes multiple electrode use indicators for various patients that the caregiver is responsible for. In this way, the caregiver can look to a single location to determine the status of the electrodes of multiple patients.

In some implementations, in addition to controlling the electrode use indicator, the electrode use indication component can be configured to perform one or more actions upon determining that an electrode patch should be removed or replaced. In some implementations, the electrode use indication component causes an email to be sent to the patient and/or a caregiver upon determining that and electrode patch should be removed or replaced. Similarly, the electrode use indicator component can be configured to cause an email to be sent when the remaining lifespan of the electrode patch is below a particular threshold (e.g., below 25% life remaining).

In some implementations, information related to the predetermined lifespan of the electrode patch can be received by entering and/or scanning an RFID ship, barcode, or other code associate with the electrode patch. For example, in some implementations, the electrode patch includes a QR code that is scanned upon installation. The QR code can indicate the predetermined lifespan of the particular electrode. In some implementations, the electrode patch includes a serial number that indicates the predetermined lifespan of the particular electrode. This information can be received by the medical device, and the electrode use indication component can access this information in determining when the predetermined lifespan of the electrode patch has been reached.

In some implementation, the electrode use indicator can provide an indication that the electrode patch should be removed or replaced so that the electrode patch is not too difficult to remove. For example, in some implementations, if an electrode patch is adhered to a patient for too long, the adhesive can become aggressive and become difficult and/or painful to remove. Thus, the electrode use indication component can suggest removal or replacement of the electrode patch while the electrode patch is still relatively easy to remove.

In some implementations, the electrode use indicator can utilize anti-tamper technology. For example, in some implementations, the electrode patch can include a mechanism for indicating whether the electrode patch has ever been applied and removed from a patient. If the electrode patch is applied to the patient, removed from the patient, and then reapplied to the patient, the mechanism can indicate that the electrode patch had been previously removed from the patient. The mechanism may cause a portion of an electrode patch surface to change color, present a symbol, and/or or present a particular message (e.g., "void," "remove or change/replace electrode," etc.).

In some implementations, the electrode use indicator is provided on the user interface of the monitor. For example, the electrode use indicator may be presented in the form of a message or a symbol on the monitor's touch screen.

In some implementations, the electrode use indication component and/or the electrode use indicator can use various other mechanisms for determining and indicating the passage of time (e.g., to determine whether the predetermined lifespan of the electrode patch has been reached). For example, in some implementations, the electrode use indicator can include a spring, weight, pendulum, or some other mechanical component to show the passage of time. In some implementations, the electrode use indicator can include an electrochemical substance that converts chemical energy into electrical energy. For example, the electrode use indicator can include a mechanism, such as a battery, that depletes or discharges at a particular rate over time. The rate of depletion and the current capacity of the battery can be used by the electrode use indicator component to infer the amount of lifespan remaining on the electrode.

In some implementations, the electrode use indicator includes a mechanism that measures a chemical reaction such as oxidation, reduction, isomerization, hydrolysis, combustion, metabolism, electroplating, photosynthesis, decomposition, a single/double displacement reaction, digestion, and/or an acid-base reaction to indicate the passage of time. For example, the chemical reaction may be started upon the electrode patch being removed from its packaging, being removed from its backing/lining, being exposed to air, being exposed to light, etc. The chemical reaction occurs over time, and the status of the chemical reaction can be used as an indicator of the amount of time passed. When a certain amount of time has passed (e.g., when the chemical reaction has reached a particular threshold), the electrode use indicator may indicate that the electrode patch should be removed or replaced.

For example, in the context of photosynthesis, two or more substances may combine to form a more complex product, and the product can be measured. In the context of a decomposition reaction, one reactant yields two or more products, and the products can be measured. In the context of a single displacement reaction, one reactant is exchanged for one ion of a second reactant, and the second reactant is measured. In the context of a double displacement reaction, two compounds exchange bonds or ions in order to form different compounds, and the resultant compounds can be measured. The double displacement reaction can be of a precipitation type (e.g., the resultant compounds are solid products), a neutralization type, or a gas formation type. In the context of a combustible reaction, a compound and an oxidant can react to produce head and oxidized products, and the oxidized products can be measured. In the context of an acid-base reaction, a hydrogen (H+) ion in an acid can react with an OH-ion in a base to form water and ionic salt which can be measured. In the context of an oxidation-reduction (redox) reaction, oxidation numbers of atoms can be changed, which may involve the transfer of electrons between chemical species, and these changes can be measured. In the context of an isomerization reaction, a structural arrangement of a compound can be changed, but its net atomic composition may remain the same. The structural arrangement and the net atomic composition can be measured. In the context of a hydrolysis reaction, a reactant can react with water, and characteristics of the reaction can be measured. In each of these examples, information related to the resulting measurements, compounds, and/or reactions is used as an indicator of the lifespan and/or the integrity of the electrode.

In some implementations, the electrode use indicator includes a mechanism that measures an endothermic or an exothermic reaction to indicate the passage of time. For example, in some implementations, the reaction may be started upon the electrode patch being removed from its packaging and/or being removed from its backing/lining. At a particular point during the reaction, such as when the mechanism has concluded or reached a particular state (e.g., reached a certain temperature), the electrode use indicator can be triggered. In the context of an endothermic reaction, heat is absorbed, thereby lowering the temperature of the mechanism's surroundings. In some implementations, the endothermic reaction involves an interaction between water and ammonium nitrate. In the context of an exothermic reaction, heat is produced, thereby raising the temperature of the mechanism's surroundings. In some implementations, the exothermic reaction involves an interaction between a supersaturated solution of sodium acetate and water and a ferrous metal embedded in the solution. Thus, in implementations that include endothermic or exothermic reactions, the temperature of the electrode use indicator and/or other portions of the electrode (or, e.g., another portion of the medical device) can be measured to determine the passage of time. Accordingly, the passage of time can be used to determine whether the predetermined lifespan of the electrode patch has been reached.

Example Infrastructure

Software running on the medical device controller (e.g., controller 120, 420 of FIGS. 1-4) can be realized by instructions that upon execution cause one or more processing devices to carry out the processes and functions described above, for example, determining whether an electrode patch should be removed or replaced, indicating an end of a predetermined lifespan of an electrode, indicating an integrity of an electrode, and/or indicating a remaining lifespan of an electrode, among others. Such instructions can include, for example, interpreted instructions such as script instructions, or executable code, or other instructions stored in a computer readable medium.

A server (e.g., the remote server 326 as shown in FIGS. 3 and 4) can be distributively implemented over a network, such as a server farm, or a set of widely distributed servers or can be implemented in a single virtual device that includes multiple distributed devices that operate in coordination with one another. For example, one of the devices can control the other devices, or the devices may operate under a set of coordinated rules or protocols, or the devices may be coordinated in another fashion. The coordinated operation of the multiple distributed devices presents the appearance of operating as a single device.

In some examples, the components of the controller 120 as shown in FIG. 3 or controller 420 of FIG. 4 may be contained within a single integrated circuit package. A system of this kind, in which both a processor (e.g., the processor 318, 418) and one or more other components (e.g., the electrode use indication component 320, 421 the cardiac event detector 324, 424 etc.) are contained within a single integrated circuit package and/or fabricated as a single integrated circuit, is sometimes called a microcontroller. In some implementations, the integrated circuit package includes pins that correspond to input/output ports (e.g., that can be used to communicate signals to and from one or more of the input/output interface devices).

Although an example processing system has been described above, implementations of the subject matter and the functional operations described above can be implemented in other types of digital electronic circuitry, or in computer software, firmware, or hardware, including the structures disclosed in this specification and their structural equivalents, or in combinations of one or more of them. Implementations of the subject matter described in this specification, such as storing, maintaining, and displaying artifacts can be implemented as one or more computer program products, i.e., one or more modules of computer program instructions encoded on a tangible program carrier, for example a computer-readable medium (e.g., the data storage 304), for execution by, or to control the operation of, a processing system. The computer readable medium can be a machine readable storage device, a machine readable storage substrate, a memory device, or a combination of one or more of them.

The term "system" may encompass all apparatus, devices, and machines for processing data, including by way of example a programmable processor, a computer, or multiple processors or computers. A processing system can include, in addition to hardware, code that creates an execution environment for the computer program in question, e.g., code that constitutes processor firmware, a protocol stack, a database management system, an operating system, or a combination of one or more of them. In some implementations, operating systems can include a Windows based operating system, OSX, or other operating systems. For instance, in some examples, the processor may be configured to execute a real-time operating system (RTOS), such as RTLinux, or a non-real time operating system, such as BSD or GNU/Linux.

A computer program (also known as a program, software, software application, script, executable logic, or code) can be written in any form of programming language, including compiled or interpreted languages, or declarative or procedural languages, and it can be deployed in any form, including as a standalone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Computer readable media suitable for storing computer program instructions and data include all forms of non-volatile or volatile memory, media and memory devices, including by way of example semiconductor memory devices, e.g., EPROM, EEPROM, and flash memory devices; magnetic disks, e.g., internal hard disks or removable disks or magnetic tapes; magneto optical disks; and CD-ROM, DVD-ROM, and Blu-Ray disks. The processor and the memory can be supplemented by, or incorporated in, special purpose logic circuitry. Sometimes a server (e.g., the remote server 326 as shown in FIGS. 3 and 4) is a general purpose computer, and sometimes it is a custom-tailored special purpose electronic device, and sometimes it is a combination of these things. Implementations can include a back end component, e.g., a data server, or a middleware component, e.g., an application server, or a front end component, e.g., a client computer having a graphical user interface or a Web browser through which a user can interact with an implementation of the subject matter described is this specification, or any combination of one or more such back end, middleware, or front end components. The components of the system can be interconnected by any form or medium of digital data communication, e.g., a communication network such as the connection between the remote server 326 and the network interface 306 shown in FIGS. 3 and 4. Examples of communication networks include a local area network ("LAN") and a wide area network ("WAN"), e.g., the Internet.

Having described several aspects of at least one example of this disclosure, the examples of the methods and apparatuses discussed herein are not limited in application to the details of construction and the arrangement of components set forth in this description or illustrated in the accompanying drawings. The methods and apparatuses are capable of implementation in other examples and of being practiced or of being carried out in various ways. Examples of specific implementations are provided herein for illustrative purposes only and are not intended to be limiting. In particular, acts, elements and features discussed in connection with any one or more examples are not intended to be excluded from a similar role in any other examples. Accordingly, the foregoing description and drawings are by way of example only Also, the phraseology and terminology used herein is for the purpose of description and should not be regarded as limiting. Any references to examples or elements or acts of the systems and methods herein referred to in the singular may also embrace examples including a plurality of these elements, and any references in plural to any example or element or act herein may also embrace examples including only a single element. References in the singular or plural form are not intended to limit the presently disclosed systems or methods, their components, acts, or elements. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms.

What is claimed is:

1. An electrode patch for use with an external medical device, the electrode patch comprising:
   a first surface configured to be attached to a skin of a patient monitored by the external medical device;
   an electrode use indication component comprising a timer and associated circuitry disposed within the electrode patch,
   wherein the associated circuitry is configured to determine an impedance of an electrical path between the first surface of the electrode and the patient when the electrode is in contact with the skin of the patient,
   wherein the associated circuitry is further configured to detect an initiating event indicating that the first surface of the electrode patch has been placed in contact with the skin of the patient to begin long-term use of the electrode patch by the patient by determining whether the impedance is within a range of impedances, and
   wherein the timer is configured to initiate a tracking of time from the initiating event in response to the determination that the impedance is within the range of impedances; and
   an indicating mechanism disposed on the electrode patch and in communication with the timer and the associated circuitry, the indicating mechanism including a light source that is configured to indicate an end of a predetermined lifespan of the electrode patch, wherein the predetermined lifespan comprises a duration measured from the initiating event indicating that the first surface of the electrode patch has been placed in contact with the skin of the patient to begin the long-term use of the electrode patch by the patient.

2. The electrode patch of claim 1, wherein the predetermined lifespan is based on a recommended wear time of the electrode patch.

3. The electrode patch of claim 1, wherein the indicating mechanism is configured to indicate that the electrode patch should be removed or replaced upon detecting the end of the predetermined lifespan of the electrode patch.

4. The electrode patch of claim 1, wherein the end of the predetermined lifespan of the electrode patch is determined based on at least one of a use or a duration of use of the electrode patch.

5. The electrode patch of claim 1, wherein the electrode patch comprises one or both of a removable electrode patch and an adhesive electrode patch.

6. The electrode patch of claim 1, wherein the indicating mechanism further comprises at least one of a display, a speaker device, and a tactile device.

7. The electrode patch of claim 1, wherein the electrode patch comprises one or more electrodes, and wherein the one or more electrodes comprises at least one sensing electrode and at least one therapy electrode.

8. The electrode patch of claim 1, wherein the indicating mechanism is configured to indicate a remaining portion of the predetermined lifespan of the electrode patch.

9. The electrode patch of claim 8, wherein the remaining portion of the predetermined lifespan is based on a measure of an integrity of the electrode patch.

10. An external medical device comprising the electrode patch of claim 1.

11. The external medical device of claim 10, wherein the duration is at least 24 hours from when the electrode patch is attached to the skin of the patient, and wherein the electrode patch is configured to indicate the end of the predetermined lifespan of the electrode patch by indicating the end of the duration.

12. The external medical device of claim 10, wherein the duration is at least one of: at least 48 hours, at least 3 days, at least one week, and at least 30 days, wherein the duration is measured from when the electrode patch is attached to the skin of the patient, and wherein the electrode patch is configured to indicate the end of the predetermined lifespan of the electrode patch by indicating the end of the duration.

13. The external medical device of claim 10, wherein the electrode patch is configured to be used for a cumulative duration of at least 24 hours from when the electrode patch is attached to the skin of the patient, and the electrode patch is configured to indicate the end of the predetermined lifespan of the electrode patch by indicating the end of the cumulative duration.

14. The external medical device of claim 10, wherein the electrode patch is configured to be used for a cumulative duration of at least one of: at least 48 hours, at least 3 days, at least one week, and at least 30 days, wherein the cumulative duration is measured from when the electrode patch is attached to the skin of the patient, and wherein the electrode patch is configured to indicate the end of the predetermined lifespan of the electrode patch by indicating the end of the cumulative duration.

15. The electrode patch of claim 1, wherein the first surface comprises at least one of a conductive layer or a conductive gel layer.

16. The electrode patch of claim 1, wherein the predetermined lifespan comprises at least one of around 7 days, around two weeks, or around 30 days.

17. The electrode patch of claim 1, wherein the light source emits light having a brightness that is indicative of an amount of time remaining on the predetermined lifespan.

18. The electrode patch of claim 1, wherein the light source emits light having a color that is indicative of an amount of time remaining on the predetermined lifespan.

19. The electrode patch of claim 18, wherein green light is indicative of the electrode patch having 80% or more of the predetermined lifespan remaining, yellow light is indicative of the electrode patch having 40-80% of the predetermined lifespan remaining, orange light is indicative of the electrode patch having 5-40% or less of the predetermined lifespan remaining, and red light is indicative of the electrode patch having 0-5% of the predetermined lifespan remaining.

20. The electrode patch of claim 1, wherein the predetermined lifespan comprises at least one of around 48 hours, around 3 days, around 4 days, around 5 days, or around 6 days.

21. The electrode patch of claim 1, wherein the range of impedances comprises a range between 100 ohms and 140 ohms.

22. The electrode patch of claim 1, wherein the range of impedances comprises a range between 20 ohms and 250 ohms.

23. An external medical device comprising:
an electrode system configured to perform at least one of 1) delivering a therapy to a patient and 2) monitoring a condition of the patient;
a removable electrode patch configured to communicate signals to or from the electrode system, the removable electrode patch comprising:
a first surface configured to be attached to a skin of the patient monitored by the external medical device;
an electrode use indication component comprising a timer and associated circuitry disposed within the removable electrode patch,
wherein the associated circuitry is configured to determine an impedance of an electrical path between the first surface of the electrode and the patient when the electrode is in contact with the skin of the patient,
wherein the associated circuitry is further configured to detect an initiating event indicating that the first surface of the electrode patch has been placed in contact with skin of the patient to begin long-term use of the removable electrode patch by the patient by determining whether the impedance is within a range of impedances, and
wherein the timer is configured to initiate a tracking of time from the initiating event in response to the determination that the impedance is within the range of impedances; and
an indicating mechanism disposed on the removable electrode patch and in communication with the timer and the associated circuitry, the indicating mechanism including a light source that is configured to indicate that the replaceable removable electrode patch has reached an end of a predetermined lifespan of the removable electrode patch, wherein the predetermined lifespan comprises a duration measured from the initiating event indicating that the first surface of the electrode patch has been placed in contact with the skin of the patient to begin the long-term use of the removable electrode patch by the patient.

24. The external medical device of claim 23, wherein the predetermined lifespan is based on a recommended wear time of the removable electrode patch.

25. The external medical device of claim 23, comprising a controller for controlling the indicating mechanism.

26. The external medical device of claim 23, wherein the removable electrode patch comprises an adhesive electrode patch.

27. An electrode patch for use with an external medical device, the electrode patch comprising:
a first surface configured for long-term continuous contact with a skin of a patient monitored by the external medical device;
an impedance circuitry disposed in contact with the first surface and configured to monitor an impedance of an interface between the electrode patch and the skin of the patient over the long-term continuous contact with the skin of the patient; and
an indicating mechanism disposed on the electrode patch and in communication with the impedance circuitry, the indicating mechanism configured to indicate a measure of an integrity of the electrode patch while the first surface of the electrode patch is in the long-term continuous contact with the skin of the patient, wherein the measure of the integrity of the electrode patch is based on the monitored impedance of the interface between the electrode patch and the skin of the patient over the long-term continuous contact with the skin of the patient,
wherein the impedance circuitry comprises a plurality of conductive elements arranged in a ring around a periphery of the electrode patch, and wherein adjacent ones of the conductive elements are electrically connected to one another along the ring.

28. The electrode patch of claim 27, wherein the indicating mechanism is configured to indicate the measure of the integrity of the electrode patch during a period of time in which the electrode patch is disposed on the skin of the patient.

29. The electrode patch of claim 27, wherein the electrode patch comprises one or both of a removable electrode patch and an adhesive electrode patch.

30. The electrode patch of claim 27, wherein the electrode patch comprises one or more electrodes, and wherein the one or more electrodes comprise at least one sensing electrode and at least one therapy electrode.

31. The electrode patch of claim 27, wherein the indicating mechanism is configured to indicate the integrity of the electrode patch based on an underlying condition of at least one of the electrode patch and an interface between the electrode patch and the skin of the patient.

32. The electrode patch of claim 31, wherein the underlying condition of the electrode patch comprises exposure to a predetermined threshold of moisture.

33. The electrode patch of claim 27, wherein the measure of the integrity of the electrode patch is based on at least one of a signal integrity and a physical integrity.

34. The electrode patch of claim 27, wherein the plurality of conductive elements establish a conductive path having a relatively low impedance when corresponding portions of the electrode patch are in a relatively high intimacy of contact with the skin of the patient.

35. The electrode patch of claim 27, wherein the long-term continuous contact comprises at least one of around 48 hours, around 3 days, around 4 days, around 5 days, or around 6 days, around 7 days, around 14 days, or around 30 days.

36. The electrode patch of claim 27, wherein the plurality of conductive elements establish a conductive path having a relatively low impedance when each conductive element of the plurality of conductive elements is in contact with the skin of the patient and having a relatively high impedance when at least one conductive element of the plurality of conductive elements is not in contact with the skin of the patient.

37. An external medical device comprising:
   an electrode system configured to perform at least one of 1) delivering a therapy to a patient and 2) monitoring a condition of the patient; and
   a removable electrode patch configured to communicate signals to or from the electrode system, the removable electrode patch comprising:
      a first surface configured for long-term continuous contact with a skin of a patient monitored by the external medical device;
      an impedance circuitry disposed in contact with the first surface and configured to monitor an impedance of an interface between the electrode patch and the skin of the patient over the long-term continuous contact with the skin of the patient; and
      an indicating mechanism disposed on the electrode patch and in communication with the impedance circuitry, the indicating mechanism configured to indicate a measure of an integrity of the electrode patch while the first surface of the electrode patch is in the long-term continuous contact with the skin of the patient, wherein the measure of the integrity of the electrode patch is based on the monitored impedance of the interface between the electrode patch and the skin of the patient over the long-term continuous contact with the skin of the patient,
      wherein the impedance circuitry comprises a plurality of conductive elements arranged in a ring around a periphery of the removable electrode patch, and wherein adjacent ones of the conductive elements are electrically connected to one another along the ring.

38. The external medical device of claim 37, comprising a garment that is adapted to be wearable on a torso of the patient.

39. The external medical device of claim 37, wherein the removable electrode patch comprises an adhesive electrode patch.

40. The electrode patch of claim 37, wherein the plurality of conductive elements establish a conductive path having a relatively low impedance when each conductive element of the plurality of conductive elements is in contact with the skin of the patient and having a relatively high impedance when at least one conductive element of the plurality of conductive elements is not in contact with the skin of the patient.

* * * * *